(12) United States Patent
Cady et al.

(10) Patent No.: US 10,131,744 B2
(45) Date of Patent: Nov. 20, 2018

(54) ANTIMICROBIAL POLYAMIDE COMPOSITIONS AND MASTITIS TREATMENT

(71) Applicants: Merial Limited, Duluth, GA (US); Genzyme Corporation, Cambridge, MA (US)

(72) Inventors: Susan Mancini Cady, Yardley, PA (US); Izabela Galeska, Newtown, PA (US); Pradeep K. Dhal, Bridgewater, NJ (US)

(73) Assignees: MERIAL INC., Duluth, GA (US); Genzyme Corporation, Cambridge, MA (US)

( * ) Notice: Subject to any disclaimer, the term of this patent is extended or adjusted under 35 U.S.C. 154(b) by 422 days.

(21) Appl. No.: 14/204,339

(22) Filed: Mar. 11, 2014

(65) Prior Publication Data

US 2014/0271526 A1    Sep. 18, 2014

Related U.S. Application Data

(60) Provisional application No. 61/790,231, filed on Mar. 15, 2013.

(51) Int. Cl.

| | |
|---|---|
| A61K 31/787 | (2006.01) |
| C08G 69/26 | (2006.01) |
| C08G 63/672 | (2006.01) |
| C08G 73/02 | (2006.01) |
| C08G 73/06 | (2006.01) |
| C07D 211/14 | (2006.01) |
| C07D 211/16 | (2006.01) |
| A61K 47/60 | (2017.01) |
| A61K 47/54 | (2017.01) |

(52) U.S. Cl.
CPC ............ *C08G 69/26* (2013.01); *A61K 31/787* (2013.01); *A61K 47/54* (2017.08); *A61K 47/60* (2017.08); *C07D 211/14* (2013.01); *C07D 211/16* (2013.01); *C08G 63/672* (2013.01); *C08G 73/028* (2013.01); *C08G 73/0273* (2013.01); *C08G 73/0627* (2013.01)

(58) Field of Classification Search
None
See application file for complete search history.

(56) References Cited

U.S. PATENT DOCUMENTS

| | | | | |
|---|---|---|---|---|
| 4,070,400 A | * | 1/1978 | Dybas | A01N 33/08 424/54 |
| 2004/0013698 A1 | * | 1/2004 | Aust | A61K 8/04 424/401 |
| 2011/0209228 A1 | | 8/2011 | Cocks | |
| 2012/0070383 A1 | | 3/2012 | Almutairi | |
| 2012/0295922 A1 | | 11/2012 | Scott | |
| 2014/0275469 A1 | | 9/2014 | Dhal et al. | |

FOREIGN PATENT DOCUMENTS

| | | |
|---|---|---|
| WO | WO 00/00023 | 1/2000 |
| WO | WO 01/93878 A2 | 12/2001 |
| WO | WO 01/96380 A2 | 12/2001 |
| WO | WO 2010/054269 A1 | 5/2010 |
| WO | WO 2012/151554 A1 | 11/2012 |
| WO | WO 2014/001353 A1 | 1/2014 |

OTHER PUBLICATIONS

Sharma et al., "Relationship of Somatic Cell Count and Mastitis: An Overview." Asian-Aust. J. Anim. Sci. vol. 24, No. 3:429-438. Mar. 2011.
Kabara et al., "Relation of Chemical Structure and Antimicrobial Activity of Alkyl Amides and Amines." Antimicrobial Agents and Chemotherapy, Dec. 1972, p. 492-498. vol. 2, No. 6.
Tumiatti et al., "Structure-Activity Relationships of Acetylcholinesterase Noncovalent Inhibitors Based on a Polyamine Backbone. 3. Effect of Replacing the Inner Polymethylene Chain with Cyclic Moieties." J. Med. Chem. 2004, 47, 6490-6498), Dec. 2004.

\* cited by examiner

*Primary Examiner* — Tigabu Kassa
(74) *Attorney, Agent, or Firm* — Judy Jarecki-Black; Patrick Lowder; Merial Inc.

(57) ABSTRACT

The present invention relates to veterinary compositions and methods of treating and/or preventing mastitis in non-human mammals. More particularly, the present invention relates to the treatment of mastitis in cows. The veterinary composition comprises a water soluble, locally-acting, antimicrobial amine functional polyamide polymer.

23 Claims, No Drawings

ANTIMICROBIAL POLYAMIDE COMPOSITIONS AND MASTITIS TREATMENT

INCORPORATION BY REFERENCE

This application claims priority to provisional application U.S. Ser. No. 61/790,231, filed on Mar. 15, 2013, which is incorporated by reference herein in its entirety. All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

This invention most generally relates to the use of water soluble, antimicrobial, amine functional polyamides in the production of safe and effective veterinary compositions. The invention further relates to using these compositions to prevent and treat mastitis in animals, including dairy cattle. It is envisioned that the compositions of the instant disclosure may also be used to prevent and treat infections caused by pathogens, which have entered animals via susceptible mucous membranes, wounds, or via post-/intra-operative procedures.

BACKGROUND OF THE INVENTION

Mastitis is the most common disease of dairy cattle. In commercial herds, the cost due to reduced milk quality can be extremely significant. This cost can be due to reduced production and the need to withhold contaminated milk from the processing stream. Mastitis is an inflammatory response of the udder tissue due to some form of injury, the most common being bacterial infection. The inflammatory response consists of an increase in blood proteins and white blood cells in the mammary tissue and the milk. The Somatic Cell Count, SCC, increases from about 200,000 SC/mL of milk (uninfected) to over 300,000 SC/mL of milk (inflamed/infected). The purpose of this response is to destroy the irritant, repair the damaged-tissue and return the udder to normal function. Inflammation is characterized by: (a) swelling of the udder where persisting inflammation leads to tissue damage and replacement of secretory tissues within the udder with nonproductive connective tissues, (b) clotting of the milk, wherein these clots are congealed leukocytes, secretory cells and protein and (c) a lower milk yield. Moreover, milk contamination exposes human consumers to diseases including tuberculosis, sore-throat, Q-fever, brucellosis, leptospirosis etc.

Mastitis begins after bacteria pass through the teat canal and enter the part of the teat known as the cistern. Significant mastitis-causing pathogens include, but are not limited to, *Staphylococcus* spp. (including *S. aureus*), *Streptococcus* spp. (including *S. agalactiae* and *S. dysgalactiae*, and *S. uberis*) and *E. coli*. There are two major periods during which this can occur: during the lactation period or during the non-lactation (dry) period. During the lactation period invasion of the teat usually occurs during milking. After milking, the teat canal remains dilated for 1-2 hours while the canal of a damaged teat may remain partially open permanently. This makes it easier for organisms from the environment or those found on injured skin to enter the teat canal. Adherence of bacteria to tissues lining cisterns and ducts may prevent flushing-out during milking and help establish infections. Bacteria eventually enter the glandular tissues where they affect alveolar cells. Toxins produced by bacteria cause death of or damage to milk-secreting epithelial cells, and these cells produce substances to the blood stream that increase blood vessel permeability. This allows leukocytes to move from the blood into the alveolus where they function by engulfing bacteria.

At the conclusion of the lactation period and once milking has stopped for the season the teat canal is closed by the formation of a natural keratin teat plug. This typically happens over a period of 2-3 weeks. However prior to the formation of this teat plug the teat canal is open and highly susceptible to bacterial infection. It can also be the case that if the teat plug is poorly developed there is an opportunity for on-going infection. Indeed it takes between one and nine weeks for most cows to form this plug and up to 5% of cows never form one. Typically 50% of teats may still be "open" at 10 days after drying off (see, e.g., Williamson J H, Woolford M W, Day A M. The prophylactic effect of a dry cow antibiotic against *Streptococcus uberis*. New Zealand Veterinary Journal (1995) 43, 228-234).

To prevent new cases of mastitis during the dry period many farmers treat cows with a prophylactic treatment of an intramammary antibiotic. This is administered in the form of a paste or gel infused with antibiotic. A syringe is used to insert the material directly into the teat canal via the opening at the base of the teat. Prevention of mastitis is reliant on sufficient antibiotic being retained in the teat canal to kill off any bacteria that may enter the teat canal over the dry period. However more recently there has been increased concern regarding the use of traditional antibiotics (e.g. beta-lactams, macrolides, and the like) in dairy cows. This is due to two reasons: (a) the potential for antibiotic residues in milk, which can cause milk processors problems in producing culture-based dairy products and (b) the potential for the development of bacterial resistance to antibiotics crossing from animal to human strains. It would therefore be highly desirable to develop new antimicrobial agents, and methods and compositions for delivering same, which do not suffer from these drawbacks, to address the costly problem of dairy cow mastitis. Such improved antimicrobial agents could equally well guard animals against a host of pathogens, including those that enter via susceptible membranes (e.g. mouth, nose, lungs, etc.), wounds, and post-operative incisions.

For additional background regarding the state-of-the art, please see US 2010/0143510 A1, to Merial Limited; U.S. Pat. No. 6,740,322 B2, to the University of Saskatchewan; and WO 2014/001353 A1, to Bayer Animal Health.

SUMMARY OF THE INVENTION

In one aspect, the invention provides safe and effective veterinary compositions comprising water soluble, antimicrobial, amine functional polyamides, having the general structure as set forth in formulae I-V. Several specific synthetic methods are also provided, but now that the genus of antimicrobial polyamides has been disclosed, the skilled person will be able to produce many other polyamide species, using routine techniques.

In another aspect, the invention provides methods of using the compositions to treat and prevent microbial infections in an animal in need thereof. In a particular embodiment, the locally-acting antimicrobial compositions are exquisitely well-adapted for the treatment and prevention of mastitis in dairy cattle.

In an embodiment, the polyamide is a compound of Formula (I):

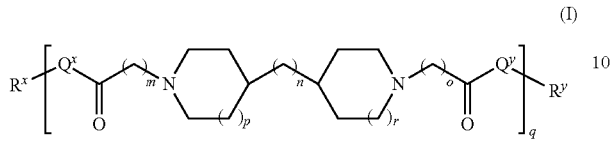

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl;
viii) $Q^y$ is NH—$R^w$, NH—$CH_2$—$R_w$, $(C_1$-$C_{10})$alkyl, or $(C_6$-$C_{14})$aryl, wherein $R^w$ is absent or a $(C_1$-$C_{10})$alkyl, $(C_2$-$C_9)$heteroalkyl, $(C_6$-$C_{14})$aryl, or $(C_2$-$C_9)$heteroaryl;
ix) $R^x$ and $R^y$ are each independently a pharmaceutically acceptable end group.

In another embodiment, the polyamide has the structure of Formula (II):

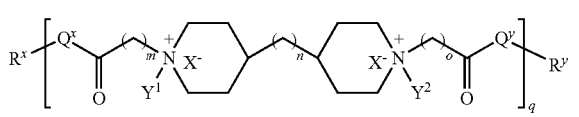

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl;
viii) $Q^y$ is NH—$R^w$, NH—$CH_2$—$R_w$, $(C_1$-$C_{10})$alkyl, or $(C_6$-$C_{14})$aryl, wherein $R^w$ is absent or a $(C_1$-$C_{10})$alkyl, $(C_2$-$C_9)$heteroalkyl, $(C_6$-$C_{14})$aryl, or $(C_2$-$C_9)$heteroaryl;
ix) $R^x$ and $R^y$ are each independently a pharmaceutically acceptable end group;
x) $X^-$ is each independently a halo or any pharmaceutically acceptable anion;
xi) $Y^1$ and $Y^2$ are each independently H or $(C_1$-$C_{10})$alkyl optionally substituted by one or more substituents selected from the group consisting of $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl, $(C_1$-$C_{10})$alkylamine, —S—O—$(C_1$-$C_{10})$alkyl, —O(O)C—$(C_1$-$C_{10})$alkyl, —$(C_1$-$C_{10})$alkyl-COOH, $(C_3$-$C_{10})$cycloalkyl-COOH, —(O)$CH_3$, —OH, amide, a dihydroxy group, represented by Formula (D),

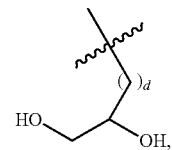

wherein d is an integer from 0 to 25, or
a polyethylene glycol group, represented by Formula (E)

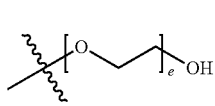

wherein e is an integer from 1 to 25.

In another embodiment, the polyamide has the structure of Formula (III):

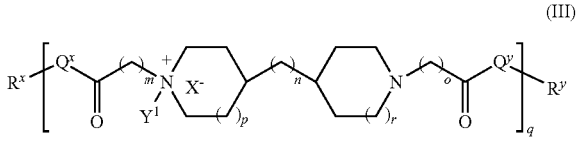

wherein:
i) m is 0, 1, 2, or 3;
ii) n is 0, 1, 2, or 3;
iii) o is 0, 1, 2, or 3;
iv) p is 0 or 1;
v) r is 0 or 1;
vi) q is an integer from 1 to 400;
vii) $Q^x$ is NH, $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl;
viii) $Q^y$ is NH—$R^w$, NH—$CH_2$—$R_w$, $(C_1$-$C_{10})$alkyl, or $(C_6$-$C_{14})$aryl, wherein $R^w$ is absent or a $(C_1$-$C_{10})$alkyl, $(C_2$-$C_9)$heteroalkyl, $(C_6$-$C_{14})$aryl, or $(C_2$-$C_9)$heteroaryl;
i) $R^x$ and $R^y$ are each independently a pharmaceutically acceptable end group;
ix) $X^-$ is a halo or any pharmaceutically acceptable anion;
x) $Y^1$ is H or $(C_1$-$C_{10})$alkyl optionally substituted by one or more substituents selected from the group consisting of $(C_1$-$C_{10})$alkyl, $(C_2$-$C_9)$heteroalkyl, $(C_3$-$C_{10})$cycloalkyl, $(C_2$-$C_9)$heterocycloalkyl, $(C_6$-$C_{14})$aryl, $(C_2$-$C_9)$heteroaryl, $(C_1$-$C_{10})$alkylamine, —S—O—$(C_1$-$C_{10})$alkyl, —O(O)C—$(C_1$-$C_{10})$alkyl, —$(C_1$-$C_{10})$alkyl-COOH, $(C_3$-$C_{10})$cycloalkyl-COOH, —(O)$CH_3$, —OH, amide, a dihydroxy group, represented by Formula (D),

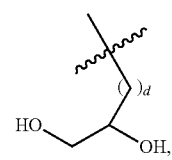

wherein d is an integer from 0 to 25, or a polyethylene glycol group, represented by Formula (E),

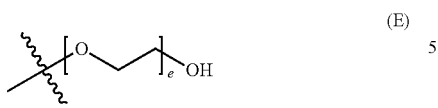

wherein e is an integer from 1 to 400.

In another embodiment, the polyamide has the structure of Formula (IV):

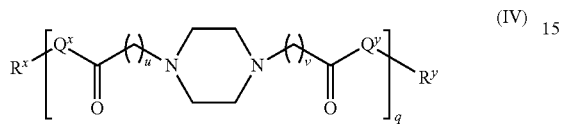

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—$CH_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
vi) $R^x$ and $R^y$ are each independently a pharmaceutically acceptable end group.

In yet another embodiment, the polyamide has the structure of Formula (V):

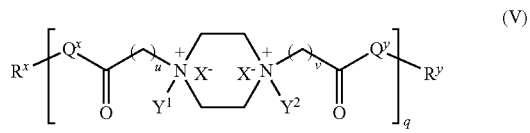

wherein:
i) u is 0, 1, 2, or 3;
ii) v is 0, 1, 2, or 3;
iii) q is an integer from 1 to 400;
iv) $Q^x$ is NH, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl;
v) $Q^y$ is NH—$R^w$, NH—$CH_2$—$R_w$, $(C_1-C_{10})$alkyl, or $(C_6-C_{14})$aryl, wherein $R^w$ is absent or a $(C_1-C_{10})$alkyl, $(C_2-C_9)$heteroalkyl, $(C_6-C_{14})$aryl, or $(C_2-C_9)$heteroaryl;
vi) $R^x$ and $R^y$ are each independently a pharmaceutically acceptable end group;
vii) $X^-$ is independently a halo or any pharmaceutically acceptable anion,
viii) $Y^1$ and $Y^2$ are independently H or $(C_1-C_{10})$alkyl optionally substituted by one or more substituents selected from the group consisting of $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —S—O—$(C_1-C_{10})$alkyl, —O(O)C—$(C_1-C_{10})$alkyl, —$(C_1-C_{10})$alkyl-COOH, $(C_3-C_{10})$cycloalkyl-COOH, —(O)$CH_3$, —OH, amide, a dihydroxy group, represented by Formula (D),

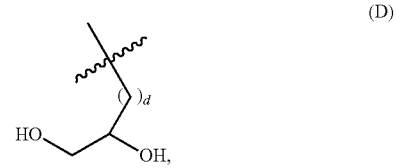

wherein d is an integer from 0 to 25, or
a polyethylene glycol group, represented by Formula (E)

wherein e is an integer from 1 to 400.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

BRIEF DESCRIPTION OF THE DRAWINGS

This disclosure contains no figures or drawings.

DETAILED DESCRIPTION OF THE INVENTION

In one aspect of the invention, veterinary compositions are provided, which comprise water soluble, antimicrobial, amine functional polyamides, and which are useful for the treatment and prevention of mastitis. The antimicrobial polyamide may be any polyamide represented by Formula I, II, III, IV, or V. In a particular embodiment, the polyamide is selected from one of the twenty-five polymers (A-Y) listed in Table 1. In addition to the particularly effective antimicrobial polyamide species presented here, a skilled person can identify additional active members of the disclosed genus with the application of non-routine experimentation.

As illustrated in the Examples below, polyamides B and C are particularly effective against a wide range of mastitis-causing pathogens, at levels as low as 0.25 μg/mL. Polyamides U and W are especially effective against *Mycoplasma bovis* (causes intractable respiratory infections, otitis media, arthritis, mastitis, and a host of other diseases in cattle), and polyamides B-D and G are especially effective against *Moraxella bovis* (causes bovine keratoconjunctivitis or "pink eye").

Importantly, the values for "MW" in Table 1 indicate the "weight average molecular weight," determined by size exclusion chromatography (SEC), which is aqueous version of GPC. As such, as used herein, for example, "polymer B" is intended to encompass compositions containing polymer B having a weight average MW of about 7.76 kDa. Moreover, "MW" is intended to mean "weight average molecular weight," unless otherwise expressly stated.

As indicated in Table 1, polymers B, C, and D each have the same repeating structure (defined herein as poly(4,4-trimethylene dipiperidine bispropanoic acid-diaminopropane)), but a different weight average MW. Moreover, the MIC data show that polymers B, C, and D tend to be comparably effective against the panel of pathogens. Thus, Applicant has shown a wide range of poly(4,4-trimethylene dipiperidine bispropanoic acid-diaminopropane) MW grades are active antimicrobial agents (i.e. MW grades from at least about 2.5 g/mol to at least about 10.6 g/ml).

As used herein, the polymers contain the following repeating units: A [4,4-trimethylene dipiperidine bispropanoic acid-4,4'-dipiperidine]; B-D [4,4-trimethylene dipiperidine bispropanoic acid-diaminopropane]; E [2,2'-bipyrrolidine bispropanoic acid-pentadiamine]; G [4,4-trimethylene dipiperidine bispropanoic acid-diaminopropane]; H [4,4-trimethylene dipiperidine bispropanoic acid-N(2-aminoethyl)-diaminoethane]; I [4,4'-trimethylene dipiperidine bispropanoic acid-N(3-aminopropyl)1,3-propane diamine]; J [4,4'-trimethylene dipiperidine bispropanoic acid-3,3'-diamino-N-methyl-dipropylamine; K [4,4'-dipiperidine bispropanoic acid-2,2'-diamino diethylamine]; L [4,4'-dipiperidine bispropanoic acid-2,2'-diamino N-methyl diethylamine]; M [4,4'-dipiperidine bispropanoic acid-3,3'-diamino-dipropylamine]; N [4,4'-dipiperidine bispropanoic acid-3,3'-diamino-N-methyl-dipropylamine]; O [4,4'-trimethylene dipiperidine-1,3-diamninopropane-N,N'-di-3-propionic acid]; P [4,4'-trimethylene dipiperidine bispropanoic acid-N,N'-dimethyl-1,3-diaminopropane]; R [4,4-trimethylene dipiperidine bispropanoic acid-4,4'-dipiperidine]; S [4,4-trimethylene dipiperidine bispropanoic acid-diaminopropane]; and T [4,4'-trimethylene dipiperidine bispropanoic acid-N-glycidol diethylene triamine].

The present invention thus provides novel and non-obvious antimicrobial polyamide compositions, and methods of using same for treating and preventing mastitis in non-human animals. The methods generally comprise administering to an infected animal an effective amount of the veterinary composition to eliminate or cure, completely or substantially, mastitis-causing pathogen(s). As detailed below, the polyamide compounds are also highly active against a broad range of other, significant, human and animal pathogens. Moreover, the polyamides have been shown to be well-tolerated in mice and rats. For example, the maximum tolerated dose for 4,4'-trimethylene dipiperidine bispropanoic acid-co-1,3-diamino propane was about 5 mg/kg (IP) and 40 mg/kg (IV).

TABLE 1

Twenty-five Antimicrobial Amine Functional Polyamides. "MW" = weight average molecular weights

| ID # | Structure | MW (kDa) |
| --- | --- | --- |
| A | 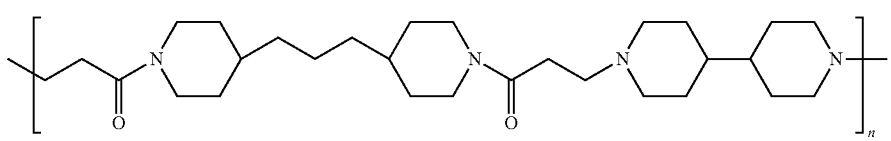 | 10.6 |
| B | 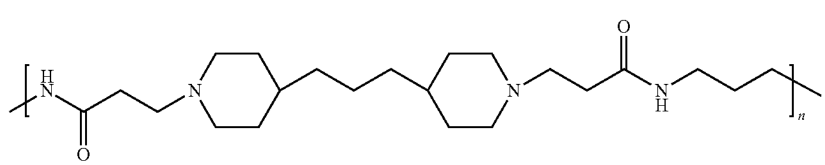 | 7.76 |
| C | 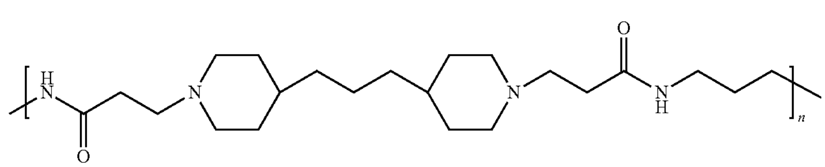 | 3.35 |
| D | 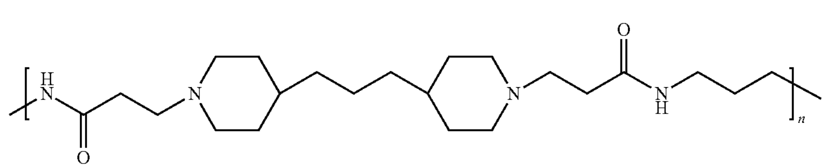 | 2.5 |

TABLE 1-continued
Twenty-five Antimicrobial Amine Functional Polyamides. "MW" = weight average molecular weights
| ID # | Structure | MW (kDa) |
|---|---|---|
| E | 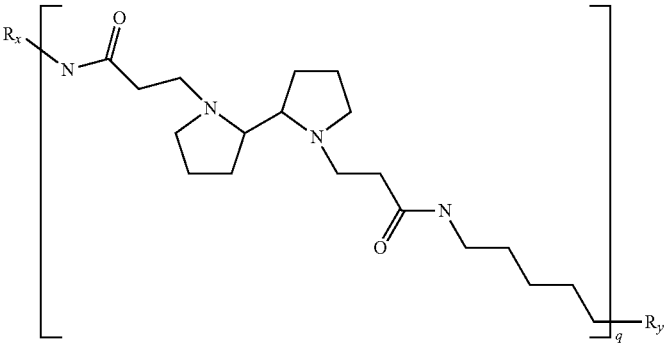 | 3.0 |
| F | 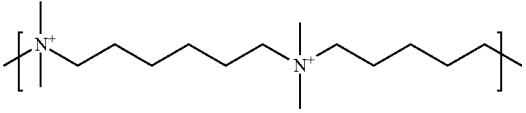 | 4.2 |
| G | 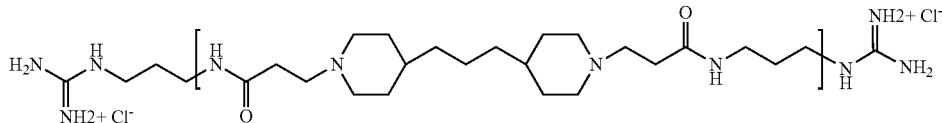 | 2.0 |
| H | 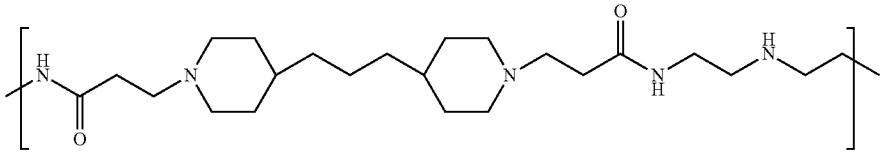 | 3-10 |
| I | 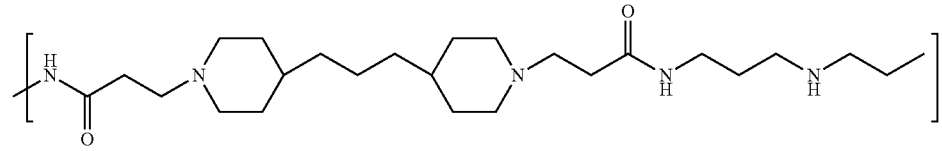 | 5.0 |
| J | 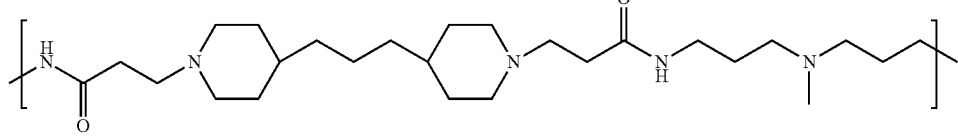 | 5.0 |
| K | 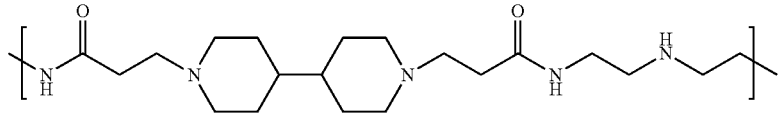 | 7.0 |
| L | 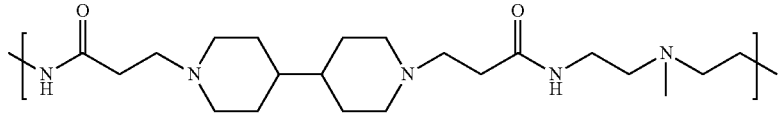 | 5.0 |
| M | 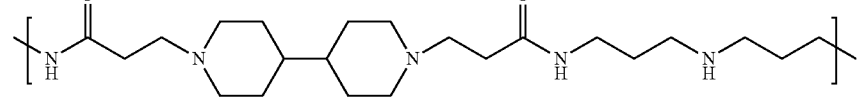 | 5.4 |

TABLE 1-continued

Twenty-five Antimicrobial Amine Functional Polyamides. "MW" = weight average molecular weights

| ID # | Structure | MW (kDa) |
|---|---|---|
| N | 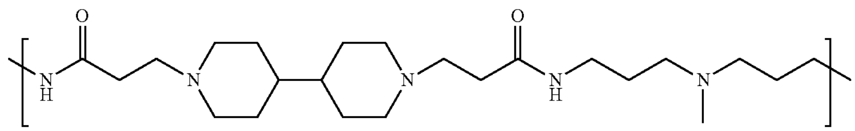 | 5.5 |
| O | 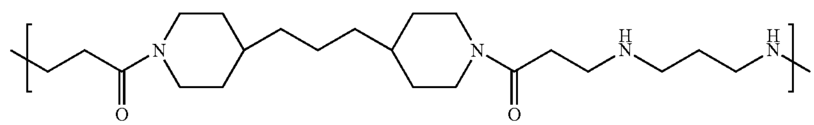 | 10.0 |
| P | 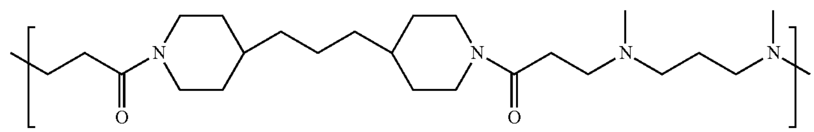 | 5.4 |
| Q | 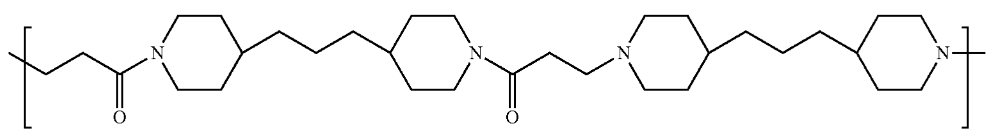 | 7.5 |
| R | 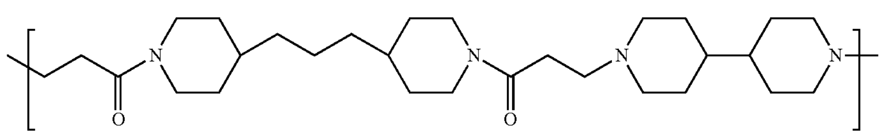 | 3-10 |
| S | 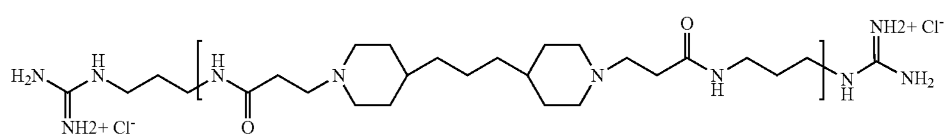 | 4.9 |
| T | 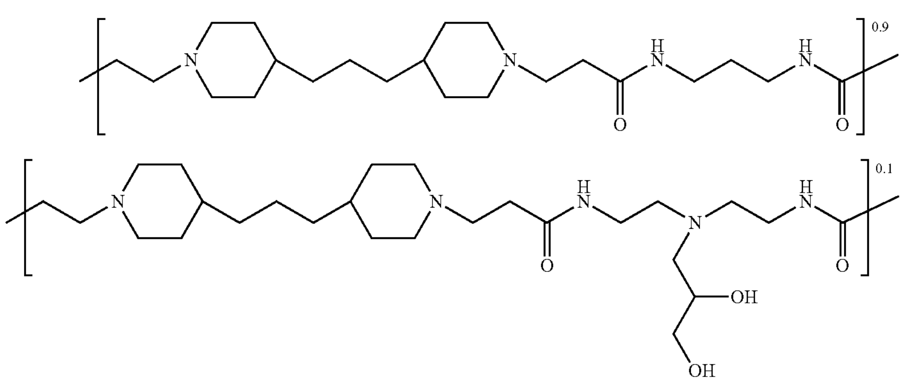 | 4.5 |
| U | 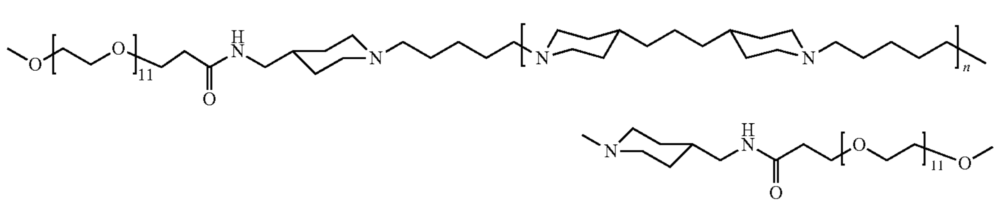 | ~10 |

TABLE 1-continued

Twenty-five Antimicrobial Amine Functional Polyamides. "MW" = weight average molecular weights

| ID # | Structure | MW (kDa) |
|---|---|---|
| V | 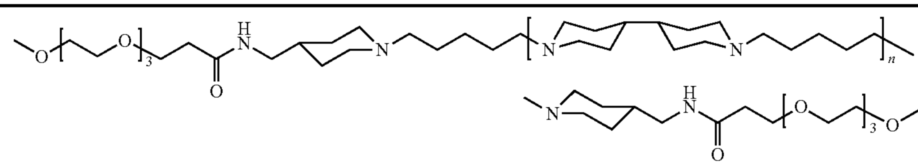 | 8.4 |
| W | | ~10 |
| X | | 5-10 |
| Y | | 5-10 |

Veterinary compositions of the invention may be in the form of thickened (or viscosity modified) solutions, gels, ointments, suspensions, pastes, or any other suitable dosage form. For example, the formulation may be a gel, which is safe and easy to administer to the teats of a dairy cow. The viscosity of such a gel may be adjusted by any veterinarily or pharmaceutically safe and effective rheology/viscosity modifier. In an embodiment, the veterinary gel may be thixotropic, in that its viscosity decreases when shear force is applied (e.g. squeezing a tube of toothpaste allows the paste to flow). Thus, in an embodiment, the compositions may be shear thinning.

In other embodiments, the compositions of the invention may include one or more additional active agent(s). For example, in cases where the composition is administered to dairy cattle at the end of lactation (i.e. beginning of the dry-period), it may be desirable to include an agent that stimulates the formation of the keratin plug. In cases where the cow's teat sphincter muscle is comprised, compositions somewhat higher viscosities may be used to improve retention in the mammary gland. The antimicrobial polymers may also be added to other currently known, or yet to be developed, dry period paste or gel compositions. The viscosity of the compositions may be measured, for example, using a Brookfield LV-E digital viscometer; different measurement speeds may be used.

The composition should ideally be sterilized to ensure good storage stability. In an embodiment, the viscosity of the pre-sterilization composition is higher than that of the post-sterilization composition, to accommodate viscosity losses that may occur during sterilization. In another embodiment, the viscosity of the pre-sterilization composition is lower, to accommodate sterilization-mediated viscosity increases.

In an embodiment, the composition viscosity is responsive or "tunable" in response to intramammary conditions, including temperature, pH, or both. In a particular embodiment, the composition viscosity increases upon exposure to pH typical of milk inside the mammary gland. In another embodiment, the composition is a heat-reversible, water-based composition, which is highly flowable before administration, but gels rapidly by the effect of the animal's udder temperature. Such situation- or environment-dependent viscosity may be accomplished by including in the composition of variety of ionic strength-, thermo- or pH-tunable polymers. Non-exhaustive examples of pH-responsive microgel rheology modifiers include powdered CARBOPOL® polymers and alkali-swellable emulsion (ASE) polymers that contain a carboxylic acid moiety. A key feature of these materials is the large increase in diameter of individual crosslinked polymer particles when the pH is raised above the pKa of the acid group. Other rheology modifiers may comprise crosslinked amphiphilic copolymers of alkyl acrylates and hydroxyalkyl esters that are activated by various surfactants.

Thus, to achieve the required rheology and viscosity properties, the composition may further comprise a veterinarily acceptable thickener or rheology modifier (TRM). TRM non-exclusively include: cellulose derivative, methyl cellulose (MC), ethylcellulose (EC), EC N50, hydroxymethyl cellulose (HMC), hydroxypropyl cellulose (HPC), hydroxypropyl methyl cellulose (HPMC), hydroxyethyl cellulose (HEC), polyethylene glycols (PEGs), poloxamers, block copolymers, cross-linked acrylic acid-based polymers, carbomers, CARBOPOL® polymers, alkali-swellable emulsion (ASE) polymers, polysaccharides, modified polysaccharides, modified starches, partially or pre-gelatinized starch, aluminum stearate, 12-hydroxystearin, THIXCIN®, beeswax, emulsifying waxes, hydrogenated peanut oil, castor oil, hydrogenated castor oil, hard/soft paraffin, metal salts of fatty acids, mucoadhesives, alkyl triammonium methosulfate, ceteraryl octanoate, polyvinyl alcohol, glycerol, chitosan, chitosan derivatives, trimethylated chitosan, xanthum gum, guar gum, hyaluronic acid, thermo-gelling agents, shear-thinning agents, shear-gelling agents, polycarbophil, polyethylene oxide, silica, fumed silica, any fumed metal oxide, non-toxic heavy metal salts, hydrogenated oils, hydrogenated castor oil and combinations thereof.

For the cellulose-based TRMs (HPMC, HEC, HPC, and the like), the gelling or thickening effect is determined by at least 1) the number of hydroxy groups available to form H-bonding; and 2) the MW of the polymer. Typically, the very high MW grade cellulose-based TRMs form significantly higher viscosity solutions, relative to their lower MW grade counterparts (given the same w/v percent in solution). The skilled person is aware of these features, and understands how to "tune" the composition viscosity to gel at any reasonable temperature. Thus, in an embodiment, the composition is so "tuned" to gel at the temperature of a lactating animal's udder.

In another embodiment, the presence of the cellulose-based TRM in the composition is associated with a slight decrease of viscosity (within the same order of magnitude) when the composition is moved from a temperature of about 20° C. to about 33° C. In such an embodiment, the composition is still very well-retained in an udder, yet at the same time, owing to its enhanced udder fluid miscibility (owing to its lowered viscosity), the API may be released relatively more quickly. The inventor's envision all manner of routinely practiced thermal-, pressure/shear-, and/or pH-tuning of the composition's viscosity may be employed to achieve the desired viscosity profile.

The composition may also be thickened to the point where it is considered a "paste." A paste consistency may be achieved by adding a sufficient amount of silica, or other suitable thickening material. Mucoadhesives and paste-forming agents may facilitate longer udder-retention times, in particular, for the "dry cow" application. In a particular embodiment, the mucoadhesive agent may be a cross-linked acrylic acid-based polymer, polycarbophil, chitosan (or derivatives thereof, such as trimethylated chitosan), polyethylene oxide, or combinations thereof.

In an embodiment, the paste composition may comprise at least one non-toxic heavy metal salt, including bismuth subnitrate. A veterinarily suitable paste may also comprise a gel base (comprising liquid paraffin), aluminum stearate and silicon dioxide. Fumed silica, such as AEROSIL®, is a particularly useful TRM and thixotropic agent. However, any veterinarily acceptable fumed metal oxide may be used in the practice of the invention.

The veterinary compositions may further comprise one or more antioxidant selected from alpha tocopherol, ascorbic acid, ascorbyl palmitate, fumaric acid, malic acid, sodium ascorbate, sodium metabisulfate, n-propyl gallate, BHA, BHT and monothioglycerol. The compositions may also comprise one or more preservatives, selected from parabens, benzalkonium chloride, benzethonium chloride, benzoic acid, benzyl alcohol, bronopol, cetrimide, chlorhexidine, chlorobutanol, chlorocresol, cresol, imidurea, phenol, phenoxyethanol, phenylethyl alcohol, phenylmercuric acetate, phenylmercuric borate, phenylmercuric nitrate, potassium sorbate, sodium benzoate, sodium propionate, sorbic acid, and thimerosal.

In a particular embodiment, the rheology modifier may be selected from 12-hydroxystearin (THIXCIN®), aluminum stearate, cellulose derivatives (e.g. hydroxypropyl cellulose (HPC); hydroxypropyl methyl cellulose (HPMC); hydroxyethyl cellulose (HEC); ethylcellulose (EC N50)), beeswax, hydrogenated peanut oil, castor oil, hard/soft paraffin, metal salts of fatty acids, and combinations thereof. As used herein, "by weight" means a percentage by weight of the total composition.

TABLE 2

Representative compositions comprising HEC

|  | % w/w | % w/w | % w/w | % w/w | % w/w |
|---|---|---|---|---|---|
| HEC (NATRASOL 250HX) | 20 | 20 | 0 | 0 | 0 |
| HEC (NATRASOL 250MX) | 0 | 0 | 25 | 25 | 15 |
| Glycerol | 80 | 40 | 75 | 35 | 35 |
| Water | 0 | 40 | 0 | 40 | 50 |

In a particular embodiment, the veterinary composition comprises hydroxypropyl methyl cellulose (HPMC), having a viscosity from about 200 cP to about 8,000 cP. In a particular embodiment, the viscosity is between about 4,000 cP to about 6,000 cP, or about 5,600 cP. A person skilled in rheology modification knows well that various composition viscosities can be achieved by varying either (or both) the polymer's molecular weight (MW) or its concentration. A particularly useful HPC is that having the CAS number 9004-65-3, although any other veterinarily-acceptable modified cellulose or starch may be used in the practice of this invention. Modified celluloses at all MW range grades (or combinations thereof) may be used to deliver the required formulation viscosity and API release profile. For example, ionic gelling agents may be used to modify API release, and extensively-crosslinked modified celluloses may be used to increase udder retention.

TABLE 3

Temperature and shear rate effect on viscosity of HPMC solutions. MW is about 86 kDa; CAS Number is 9004-65-3

|  | Bath Temp (° C.) | Speed (rpm) | Torque (%) | Viscosity (cps) |
|---|---|---|---|---|
| A0263-69A | 20 | 3 | 44.9 | 4479 |
| (2% HPMC in H$_2$O) | 20 | 6 | 84.8 | 4239 |
|  | 25 | 3 | 35.2 | 3519 |
|  | 25 | 6 | 66.9 | 3344 |
|  | 33 | 3 | 24.9 | 2499 |
|  | 33 | 6 | 47.0 | 2354 |
| A0263-69B | 20 | 3 | 14.5 | 1450 |
| (~1.6% HPMC in H$_2$O) | 20 | 6 | 28.1 | 1405 |
|  | 25 | 3 | 11.0 | 1090 |
|  | 25 | 6 | 23.1 | 1160 |
|  | 33 | 3 | 7.0 | 690 |
|  | 33 | 6 | 14.6 | 725 |

Thickened aqueous solutions of hydroxypropyl cellulose (HPC/KLUCEL) were evaluated as viscosity modifiers of aqueous solutions. As indicated in Table 4, the viscosity of the solution can be modulated by the concentration and grade (i.e. MW) of polymer.

TABLE 4

Viscosity (in cP) of aqueous KLUCEL ® solutions, measured at either 25 or 33° C.

| KLUCEL Solution | Viscosity at 25° C. (cP) | Viscosity at 33° C. (cP) |
|---|---|---|
| EF 2.5% | <20 | <20 |
| EF 5% | <20 | <20 |
| EF 10% | ~400 | ~300 |
| GF 1% | <10 | <10 |
| GF 2.5% | ~360 | ~210 |
| GF 5% | ~1120 | ~900 |
| ELF 2.5% | <5 | <5 |
| ELF 5% | <10 | <5 |
| ELF 10% | ~200 | ~140 |

In another embodiment, the veterinary composition further comprises a poloxamer, which is a triblock copolymer of polyethylene oxide, polypropylene oxide$_b$-polyethylene oxide$_a$ [PEO$_a$-PPO$_b$-PEO$_a$]. Various members of this class of polymer, e.g., POLOXAMER 188 and POLOXAMER 407, show inverse thermosensitivity within the physiological temperature range. Thus, these polymers are soluble in aqueous solutions at low temperature, but gel at higher temperatures. POLOXAMER 407 is a biocompatible polyoxpropylene-poloxyethylene block copolymer having an average molecular weight of about 12,500 and a polyoxypropylene fraction of about 30%. Such reversibly gelling systems are useful wherever it is desirable to handle a material in a fluid state, but performance is preferably in a gelled or more viscous state.

In another embodiment, the veterinary composition comprises a veterinarily acceptable mineral oil or esters of fatty acids from natural origin, or a mixture thereof, which are suitable for carrying the antimicrobial polyamide, and which are fully acceptable for intramammary infusion.

Mineral oils are mixtures of liquid hydrocarbons known in medicine as liquid paraffin, light liquid paraffin or petroleum, for example, those of the United States Pharmacopoeia (USP) or British Pharmacopoeia (BP). Especially good results have been achieved with liquid paraffin. Liquid paraffin (mineral oil) is a mixture of liquid saturated hydrocarbons from petroleum.

Esters of fatty acids that come from natural origin are conveniently prepared by the fatty acids followed by esterification of these acids with a given alcohol. Fractionated vegetable oil having the desired compositions are commercially available. For example, MIGLYOL® 812 (capric/caprylic triglycerides) and MIGLYOL® 840 (propylene glycol dicaprylate/caprate).

In one embodiment, the veterinary composition comprises microcrystalline wax, oleoyl polyoxylglyceride, and cottonseed oil. In yet another embodiment, the composition comprises hydrogenated peanut oil, aluminum monostearate, and peanut oil. Where an emulsion is desired (e.g. to incorporate an oily component), surfactants including oleoyl polyoxyl-6 glycerides, may be added to the composition. Thus, in an embodiment, the composition may be an emulsion, wherein the API antimicrobial polymer is dissolved in the aqueous phase.

Additionally, the formulations may contain other non-API ingredients, such as pH modifiers, antioxidants, preservatives, and colorants. These compounds are well known in the formulation art. Antioxidant such as an alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01% to about 2.0%, based upon total weight of the formulation, with about 0.05% to about 1.0% being especially preferred. Preservatives, such as the parabens (methylparaben and/or propylparaben), are suitably used in the formulation in amounts ranging from about 0.01% to about 2.0%, with about 0.05% to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Ranges for these compounds include from about 0.01% to about 5% (w/w) of the final composition. Colorants may also be added to facilitate complete application of the formulation and visualization of retention in the udder, or marking of the infected quarter. Preferred ranges include from about 0.5% to about 25% (w/w).

In another embodiment, the polyamide composition is effective against otitis in companion animals, including canines Veterinary compositions comprising any one of polymers B to D show good efficacy against *Staphylococcus* spp., which are normally found in the ears of canines. The polymers are water soluble and can be easily formulated in vehicles with adhesive or in situ gelling properties (e.g. thermo-tunable polymers). Thus, a particular embodiment of the invention provides an ointment (or other suitably adhesive polyamide composition), which may gel on contact with an ear canal, for treating canine or feline otitis.

In an embodiment, the composition may be formulated as a spray or adhesive strip, for pink eye and other indications requiring external application. The spray may comprise a mucoadhesive agent, a viscosity modifier, a fast evaporating solvent component, or combinations thereof. The spray may be formulated to gel after the solvent has evaporated. In an embodiment, an adhesive strip (e.g. a reservoir or matrix) may be applied near and/or above the target area (e.g. the eye, in pink eye), to allow the API to release in a controlled and/or extended manner.

"Substituted" means the substitution of a carbon in alkyl, heterocyclic or aryl groups with one or more non-carbon substituent. Non-carbon substituents are selected from nitrogen, oxygen and sulfur.

"Unsubstituted" means the group is comprised of only hydrogen and carbon.

The term "polymer" means a molecule comprised of repeating units. The term "repeat unit" or "monomer" means a group in a polymer that repeats or appears multiple times in a polymer. A polymer may be a copolymer if the repeating units or "comonomers" are chemically and structurally different from one another.

The term "pharmaceutically acceptable anion" means an anion that is suitable for pharmaceutical use. Pharmaceutically acceptable anions include but are not limited to halides, carbonate, bicarbonate, sulfate, bisulfate, hydroxide, nitrate, persulfate, sulfite, acetate, ascorbate, benzoate, citrate, dihydrogen citrate, hydrogen citrate, oxalate, succinate, tartrate, taurocholate, glycocholate, and cholate.

The term "pharmaceutically acceptable end group" means an end group that is suitable for pharmaceutical use. Examples of pharmaceutically acceptable end groups include but are not limited to H, $(C_1-C_{10})$alkyl, $(C_2-C_9)$heteroalkyl, $(C_3-C_{10})$cycloalkyl, $(C_2-C_9)$heterocycloalkyl, $(C_6-C_{14})$aryl, $(C_2-C_9)$heteroaryl, $(C_1-C_{10})$alkylamine, —O(O)C—$(C_1-C_{10})$alkyl, $(C_1-C_{10})$alkyl-COOH, $(C_3-C_{10})$cycloalkyl-COOH, —(O)CH$_3$, —OH, amide, a guanidino group, a guanidinium chloride group, a guanidinobenzene group, a dihydroxy group, and a polyethylene glycol group.

The term "effective amount" of a disclosed amine functional polyamides is a quantity sufficient to achieve a therapeutic and/or prophylactic effect on the particular condition being treated, such as an amount which results in the prevention or a decrease in the symptoms associated with mastitis. The precise amount of the disclosed amine functional polyamides that is administered will depend on the type and severity of mastitis or infection being treated and on the characteristics of the animal, such as general health, age, body weight and tolerance to drugs.

The present invention is thus, in a particular embodiment, directed to veterinary polyamide compositions, and the use of these compositions to prevent or treat mastitis in a non-human milk-producing mammal. The veterinary compositions are well-suited for intra-mammary (IMM) administration, during the wet or dry period. The compositions are especially well-suited to IMM application because the antimicrobial polyamides are substantially unable to cross the "milk blood barrier" (due to their charge and relatively large molecular weight). For example, the average molecular weight of "polymer B" polyamides is greater than 10-fold higher than that of ceftiofur, which is a well-known, systemically acting antibiotic. Drugs that do move across the blood-milk barrier typically do so via passive diffusion. At the milk pH of about 6.4 to about 6.8, the end groups of the antimicrobial polymers should remain charged, thus excluding them from the systemic circulation.

In one embodiment of the method, an effective amount of the polyamide composition is administered IMM to an infected animal to produce in the animal a non-systemic/local polyamide exposure level that is sufficient to eliminate or cure the mastitis-causing infection. In a particular embodiment, the local (e.g. teat canal) exposure levels are sufficient to completely eliminate or cure the microbial infections. In a more particular embodiment, the polyamide remains sufficiently non-systemic such that only a minimal milk withdrawal time is required. In an even more particular embodiment, milk need only be withdrawn for less than about twenty-four hours. Ideally, about zero milk withdrawal time is required following treatment of teat canals with the locally-acting polyamide compositions.

According to another aspect of the present invention, a method for treating mastitis is provided, comprising administering to a non-human mammal having mastitis an effective amount of a veterinary composition comprising an amine functional polyamide polymer.

According to still another aspect of the present invention a method for preventing mastitis is provided, comprising administering to a non-human mammal an effective amount of a veterinary composition comprising an antimicrobial amine functional polyamide polymer.

According to another aspect of the present invention, a use of a veterinary composition comprising an antimicrobial amine functional polyamide for the treatment or prevention of mastitis on a non-human mammal is provided.

According to yet another aspect of the present invention, a use of an amine functional polyamide for the manufacture of an intra-mammary veterinary composition for the treatment or prevention of mastitis in a non-human mammal is provided.

According to a particular embodiment of the use for manufacture, a composition, preferably a veterinary composition, comprising an antimicrobial amine functional polyamide.

As used herein, "completely curing" mean that a given treatment regimen has resulted in substantial reduction of the infecting pathogen(s), and that the clinical signs owing to the pathogen(s) do not return. For example, a bovine "completely cured" of the bacteria (that caused the mastitis) will recover to having lower than 300,000 SC/mL of milk. Since SCC is indicative of the animal's own immune response against the pathogen, it is expected that the SCC will remain at "peak mastitis levels" for some period of time after the composition has cured the infection. Thus, when post-treatment SCC concentrations are recited herein, it is assumed that a sufficient period of time has elapsed for the bovine to return to a pre-infection, baseline SCC milk concentration. The baseline SCC may vary among breeds, and among members of a single breed, but the skilled person will be able to assess whether a given post-treatment SCC is consistent with an infected versus a non-infected bovine.

In a particular embodiment, a completely cured bovine has fewer than 250,000 SC/mL. In an even more particular embodiment, after a suitable amount of recovery time (post-treatment), a completely cured bovine has no more than about 200,000 SC/mL of milk. In any event, a bovine post-treatment will have about the same SC/mL as its non-infected cohorts (e.g. co-housed dairy cattle of about the same breed and about the same age).

Pharmaceutical Compositions

In accordance with the present invention, the veterinary composition used in this treatment comprises a water soluble, antimicrobial polyamide polymer. Particularly effective polyamides include polymers B, C, D, U, and T.

The veterinary composition is intended to be a locally-acting, intra-mammary product. Preferred intra-mammary antimicrobial polyamides do not enter the systemic circulation, or only do so to a vanishingly small extent. In one embodiment, the veterinary composition is an intra-mammary product that is administered via the teat orifice to treat or prevent mastitis of a non-human, milk-producing mammal.

As used herein, the term "veterinarily effective amount" refers to a dose sufficient to either prevent or treat mastitis in an animal to which the composition is administered. The dose depends on the active ingredient(s), the animal being treated, the state of condition, and the severity of the conditions. The determination of those factors is well within the level of one skilled in the art. The present invention is preferably prepared as an intra-mammary ointment, suspension, solution or gel.

Methods

The veterinary composition of the present invention may be used in the prevention or for the treatment of mastitis in an animal. Mastitis may be associated with several pathogens including *E. coli, Klebsiella* spp., *Enterobacter* spp., *Salmonella* spp., *Citrobacter* spp., *Serratia* spp., *Shigella* spp., *Edwardsiella* spp., *Hafnia* spp., *Morganella* spp., *Providencia* spp., *Yersinia* spp., *Staphylococcus aureus, Staphylococcus* spp., *Pseudomonas* spp., *Streptococcus agalactiae, Streptococcus dysgalactiae, Streptococcus* spp., *Enterococci, Corynebacterium* spp., *Arcanobacterium* spp., *Actinomyces* spp., *Mycobacterium* spp., *Prototheca* spp., *Mycoplasma* spp., *Erwinia* spp., *Lactobacillus* spp., among others.

The composition may also be used in the prevention or for the treatment of infections caused by other pathogens, in other animals.

The veterinary composition may be used for various applications with the application route and dosage regimen dictated by the frequency of milking and/or the condition of the mammary gland of the animal.

The veterinary composition can be applied to all non-human milk producing mammals that need treatment or prevention of mastitis, such as cattle, camel, buffalo, goat or sheep, however it is especially important in ruminants that are used for milk production for human consumption such as cattle, buffalo, sheep, and goat.

Treatment of mastitis is curing or ameliorating an animal that has contracted mastitis, i.e. reducing at least one symptom of mastitis. Mastitis refers to inflammation of the mammary gland. Physical, chemical and usually bacteriological changes in the milk and pathological changes in the glandular tissue characterize it. The glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. An inflamed udder can be visibly seen or determined through palpation of the udder. In many cases the diagnosis of subclinical infections has come to depend largely on indirect tests which depend on the leukocyte content of the milk (flakes, clots, or serous milk), at least 1 bacterium is detected in at least 100 mL of milk from the udder, elevated somatic cell count (SCC) usually higher than 300,000 cells/mL and/or the electrical conductivity of the milk is increased from normal. Prevention of mastitis means preventing the occurrence of the infection. Prevention also includes treatment of cows that do not exhibit any signs of mastitis but are in the presence of other cows that do have at least one sign of mastitis to minimize or prevent the transmission or potential transmission of mastitis from one cow to another.

The effectiveness of the veterinary composition in treating mastitis of an animal is quantified as the percent of cleared mammary glands (i.e., milk from one teat is free from any bacteria). In one embodiment, the veterinary composition clears at least 50% of the mammary glands of the animal. In another embodiment, the veterinary composition clears from about 50% to about 100% of the mammary glands of the animal. In yet another embodiment, the veterinary composition clears from about 75% to about 100% of the mammary glands of an animal.

The veterinary composition may be administered intra-mammarily (IMM), through the teat orifice into the interior cavity of the mammary gland and its associated ductal system. The veterinary composition may be in the form of an ointment, suspension, solution or gel.

The dose of the polyamide for the treatment of one udder quarter may contain from about 20 to about 3000 mg of the polyamide; from about 100 to about 2000 mg; from about 200 to about 1500 mg; from about 250 to about 1000 mg; from about 300 to about 500 mg; or about 300 mg.

The treating or preventing dose may be administered repeatedly over a period of from one to eight days. In one embodiment, the dose is administered once or twice a day over a period of two to eight days. In another embodiment, the dose is administered once or twice a day over a period of four to six days. It is believed that the precise combination of dosage and timing will be subject to a wide range of variation and that numerous combinations effective in treating or preventing a disease can be readily established by those of ordinary skill in the art in view of the present disclosure.

In view of the above, it will be seen that the several objects of the invention are achieved and other advantageous results attained. As various changes could be made in the above formulations, products, and processes without departing from the scope of the invention, it is intended that all matter contained in the above description and shown in the accompanying tables shall be interpreted as illustrative and not in a limiting sense.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements. Moreover, the term "consisting essentially of" is intended to mean that there may be additional elements other than the listed elements, but not ones that would be considered "active ingredients" (e.g. non-active excipients). And finally, the term "consisting of" is intended to mean that only the listed elements are included.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The following examples are simply intended to further illustrate and explain the present invention. The examples, therefore, should not be regarded as limiting the scope of the invention or manner in which it may be practiced.

EXAMPLES

Example 1. Minimum Inhibitory Concentration (MIC) in Broth

The antimicrobial efficacy of twenty-five antimicrobial polymers (and Erythromycin) was evaluated using an MIC assay. For each study, a doubling dilution concentration of each antimicrobial polymer was prepared at 2× the final concentration range (0.12 to 16 µg/mL), and 100 µL of the API-null formulation was dispensed into the negative control wells. Overall, the antimicrobial polymer-containing compositions performed comparably well, or better, against the pathogens, as compared to Erythromycin (ERY).

TABLE 5A

Description of bacteria, media and incubation conditions for MIC tests

| | | Susceptibility Testing Information | | |
|---|---|---|---|---|
| | | | Incubation | |
| Organism | Media | Temperature (° C.) | Atmosphere | Time (hr) |
| Actinobacillus pleuropneumoniae | VFM | 36 ± 2 | 5 ± 2% $CO_2$ | 20-24 |
| Bordetella bronchiseptica | MHB | 36 ± 2 | Aerobic | 16-20 |
| Enterobacter species | MHB | 36 ± 2 | Aerobic | 16-20 |
| Escherichia coli | MHB | 36 ± 2 | Aerobic | 16-20 |
| Histophilus somni | VFM | 36 ± 2 | 5 ± 2% $CO_2$ | 20-24 |
| Klebsiella species | MHB | 36 ± 2 | Aerobic | 16-20 |
| Mannheimia haemolytica | MHB | 36 ± 2 | Aerobic | 18-24 |

TABLE 5A-continued

Description of bacteria, media and incubation conditions for MIC tests

| | | Susceptibility Testing Information | | |
|---|---|---|---|---|
| | | | Incubation | |
| Organism | Media | Temperature (° C.) | Atmosphere | Time (hr) |
| Moraxella bovis | MHB | 36 ± 2 | Aerobic | 16-24 |
| Mycoplasma bovis | HBAN | 36 ± 2 | Aerobic | 20-24 |
| Pasteurella multocida (Canine and BRD) | MHB | 36 ± 2 | Aerobic | 18-24 |
| Proteus mirabilis | MHB | 36 ± 2 | Aerobic | 16-20 |
| Pseudomonas aeruginosa | MHB | 36 ± 2 | Aerobic | 16-20 |
| Serratia marcescens | MHB | 36 ± 2 | Aerobic | 16-20 |
| Staphylococcus aureus (including MRSA) | MHB | 36 ± 2 | Aerobic | 16-20 |
| Staphylococcus pseudintermedius (including MRSP) | MHB | 36 ± 2 | Aerobic | 16-20 |
| Coagulase negative Staphylococcus species | MHB | 36 ± 2 | Aerobic | 16-20 |
| Streptococcus agalactiae | LHB | 36 ± 2 | Aerobic | 20-24 |
| Streptococcus canis | LHB | 36 ± 2 | Aerobic | 20-24 |
| Streptococcus dysgalactiae | LHB | 36 ± 2 | Aerobic | 20-24 |
| Streptococcus uberis | LHB | 36 ± 2 | Aerobic | 20-24 |

MHB = Mueller Hinton Broth, LHB = Mueller Hinton broth with 3% lysed horse blood, VFM = Veterinary Fastidious media, HBAN = Modified Hayflick's broth with Alamar Blue ® and β-NAD

TABLE 5B

Additional bacterial details

| ID # | Sample ID | Source | Isolate ID | Disease/ Animal |
|---|---|---|---|---|
| 1-10 | N/A | Various | E. coli | Mastitis |
| 11-20 | Wound | Canine | E. coli | Pet |
| 21-27 | N/A | CO Dairy | Enterobacter spp. | Mastitis |
| 28-32 | N/A | CO Dairy | Klebsiella spp. | Mastitis |
| 33 | N/A | CO Dairy | K. oxytoca (SIM 0.38) | Mastitis |
| 34-35 | N/A | CO Dairy | K. oxytoca | Mastitis |
| 36-37 | N/A | CO Dairy | K. pneumoniae | Mastitis |
| 38-47 | N/A | Various | K. pneumoniae | Pet |
| 48-57 | Wound | Canine | Proteus mirabilis | Pet |
| 58-67 | Wound | Canine | P. aeruginosa | Pet |
| 68-77 | N/A | Various | Serratia marcescens | Mastitis |
| 78-87 | Lung, Respiratory | Canine/ Feline | B. bronchiseptica | Pet |
| 88-97 | N/A | Various | Moraxella bovis | Bovine |
| 98 | N/A | Various | S. aureus | Mastitis |
| 108-122 | Human (Various) | N/A | MR S. aureus | Human |
| 123 | Canine nose | N/A | MR S. aureus | Pet |
| 124-127 | Human | N/A | MR S. aureus | Human |
| 128-137 | Wound | Canine | S. intermedius | Pet |
| 138-147 | Canine | ISU | MR S. pseudintermedius | Pet |
| 148-157 | N/A | CO Dairy | Coagulase-negative Staph | Mastitis |
| 158-167 | N/A | Various | M. haemolytica | BRD |
| 168-177 | Wound | Canine | P. multocida | Pet |
| 178-187 | N/A | Various | P. multocida | BRD |
| 188-197 | N/A | CO Dairy | Strep. agalactiae | Mastitis |
| 198-207 | Wound | Canine | Strep. canis | Pet |
| 208-213 | N/A | Various | Strep. dysgalactiae | Mastitis |
| 214 | N/A | ISU | Strep. dysgalactiae | Bovine Joint |
| 215-216 | N/A | N/A | Strep. dysgalactiae | Mastitis |
| 217 | N/A | Canine | Strep. dysgalactiae | Pet |
| 218-227 | Bovine | Various | Strep. uberis | Mastitis |
| 228-237 | Porcine Lung | Various | A. pleuropneumoniae | SRD |
| 238-247 | N/A | Various | Histophilus somni | BRD |
| 248-257 | 7368 | CO Dairy | Mycoplasma bovis | Mastitis |

TABLE 6-1

MIC (μg/mL) of 26 compounds against selected bacteria

| Compound | S. aureus (Sta-3) ATCC 29213 MIC (μg/mL) | S. aureus Known range | E. faecalis (Str-15) ATCC 29212 MIC (μg/mL) | E. faecalis Known range | S. pneumoniae (Str-53) ATCC 49619 MIC (μg/mL) | S. pneumoniae Known range | M. bovis (MB-1) ATTC 25523 MIC (μg/mL) | A. pleuro. (AC-1) ATTC 27090 MIC (μg/mL) | H. somni (H-15) ATTC 700025 MIC (μg/mL) |
|---|---|---|---|---|---|---|---|---|---|
| A | 16 | — | 16 | — | 16 | — | 8 | >16 | >16 |
| B | 2 | — | 2 | — | 2 | — | >16 | >16 | >16 |
| C | 1 | — | 1 | — | 2 | — | >16 | >16 | >16 |
| D | 2 | — | 2 | — | 4 | — | >16 | >16 | >16 |
| E | >16 | — | >16 | — | >16 | — | >16 | >16 | >16 |
| F | 8 | — | >16 | — | >16 | — | >16 | >16 | >16 |
| G | 2 | — | 4 | — | 4 | — | >16 | >16 | >16 |
| H | 4 | — | 8 | — | 16 | — | >16 | >16 | >16 |
| I | 2 | — | 8 | — | >16 | — | >16 | >16 | >16 |
| J | 4 | — | >16 | — | 16 | — | >16 | >16 | >16 |
| K | 4 | — | 16 | — | >16 | — | >16 | >16 | >16 |
| L | 16 | — | >16 | — | >16 | — | >16 | >16 | >16 |
| M | 4 | — | >16 | — | >16 | — | >16 | >16 | >16 |
| N | 4 | — | 16 | — | >16 | — | >16 | >16 | >16 |
| O | 8 | — | 16 | — | 16 | — | >16 | >16 | >16 |
| P | >16 | — | >16 | — | >16 | — | >16 | >16 | >16 |
| Q | >16 | — | 16 | — | 8 | — | 4 | >16 | >16 |
| R | >16 | — | 16 | — | 16 | — | 8 | >16 | >16 |
| S | 2 | — | 2 | — | 2 | — | >16 | >16 | >16 |
| T | 2 | — | 2 | — | 2 | — | >16 | >16 | >16 |
| U | 8 | — | 4 | — | 2 | — | 2 | >16 | >16 |
| V | 4 | — | 8 | — | 16 | — | >16 | >16 | >16 |
| W | 4 | — | >16 | — | >16 | — | 0.5 | >16 | >16 |
| X | 8 | — | 8 | — | 8 | — | >16 | >16 | >16 |
| Y | 4 | — | >16 | — | >16 | — | >16 | >16 | >16 |
| Ery | 0.5 | 0.25-1 | 2 | 1-4 | 0.06 | .03-.12 | 4, >8 | 8 | 1 |

TABLE 6-2

MIC against *Actinobacillus pleuropneumoniae*

| # | Compounds A-Y | Erythromycin (Ery) |
|---|---|---|
| 228-231, 235 | >16 | 4 |
| 232-236 | >16 | 8 |
| 237 | >16 | 2 |

TABLE 6-3

MIC against *Bordetella bronchiseptica*

| # | A, C-F, H-O, R-T W, Y | B | G | P, Q | U | V | X | Ery |
|---|---|---|---|---|---|---|---|---|
| 78 | >16 | 16 | 8 | 16 | 16 | 16 | 8 | 8 |
| 79 | >16 | 8 | 8 | 16 | 16 | 16 | 8 | 8 |
| 80 | >16 | 16 | 8 | 16 | 8 | 16 | 8 | 2 |
| 81 | >16 | 8 | 8 | 16 | 16 | 16 | 8 | 8 |
| 82 | >16 | 8 | 8 | 16 | 8 | 16 | 8 | 2 |
| 83 | >16 | 16 | 8 | 16 | 8 | 8 | 8 | 8 |
| 84 | >16 | 8 | 16 | 16 | 8 | 8 | 8 | 8 |
| 85 | >16 | 8 | 8 | 16 | 8 | 16 | 8 | >8 |
| 86 | >16 | 16 | 16 | 16 | 8 | 16 | 8 | >8 |
| 87 | >16 | 8 | 8 | 8 | 8 | 16 | 8 | 8 |

TABLE 6-4

MIC against *Enterobacter* species

| # | A | B | C | D | E, K-M | F | G | H, P, X | I | J | N | O, Q | R | S,T | U | V, Y | W | Ery |
|---|---|---|---|---|---|---|---|---|---|---|---|---|---|---|---|---|---|---|
| 21 | 8 | 4 | 4 | 8 | >16 | 8 | 4 | 8 | 8 | 8 | 16 | 8 | 16 | 4 | 8 | 8 | 16 | >8 |
| 22 | >16 | 2 | 2 | 4 | >16 | 8 | 4 | 8 | 8 | 8 | 16 | 16 | 16 | 4 | 4 | 16 | 8 | >8 |
| 23 | 16 | 2 | 2 | 4 | >16 | >16 | 4 | 8 | 8 | 8 | 16 | 8 | 8 | 4 | 4 | 8 | 16 | >8 |
| 24 | 16 | 4 | 2 | 4 | >16 | 8 | 4 | 8 | 4 | 8 | 8 | 8 | 16 | 2 | 4 | 8 | 8 | >8 |
| 25 | 16 | 2 | 2 | 4 | >16 | 16 | 4 | 8 | 4 | 8 | 16 | 8 | 16 | 2 | 4 | 8 | 8 | >8 |
| 26 | 16 | 2 | 2 | 4 | >16 | 16 | 4 | 8 | 4 | 4 | 8 | 8 | 16 | 2 | 4 | 8 | 16 | >8 |
| 27 | 8 | 2 | 2 | 2 | >16 | 8 | 2 | 8 | 4 | 4 | 8 | 8 | 16 | 2 | 2 | 8 | 16 | >8 |

TABLE 6-5

MIC against *Escherichia coli*

| # | A | B | C | D | E, L, M | F | G | H | I | J | K | N |
|---|---|---|---|---|---------|---|---|---|---|---|---|---|
| 1 | 8 | 4 | 4 | 8 | >16 | 8 | 4 | 8 | 8 | 8 | 16 | 16 |
| 2 | 8 | 4 | 4 | 8 | >16 | 8 | 8 | 8 | 8 | 16 | 16 | 16 |
| 3 | 16 | 4 | 4 | 8 | >16 | 8 | 8 | 8 | 8 | 8 | 16 | 16 |
| 4 | 16 | 4 | 4 | 8 | >16 | 16 | 8 | 8 | 16 | 16 | 16 | 16 |
| 5 | 8 | 4 | 4 | 8 | >16 | 8 | 4 | 8 | 8 | 8 | 16 | 16 |
| 6 | 8 | 4 | 4 | 8 | >16 | 8 | 8 | 8 | 8 | 16 | 16 | 8 |
| 7 | 16 | 4 | 8 | 16 | >16 | 16 | 8 | 8 | 8 | 8 | >16 | 16 |
| 8 | 16 | 2 | 2 | 4 | >16 | 16 | 4 | 8 | 8 | 8 | 8 | 16 |
| 9 | 8 | 4 | 4 | 8 | >16 | 16 | 4 | 8 | 8 | 16 | 16 | 16 |
| 10 | 16 | 2 | 2 | 4 | >16 | 8 | 4 | 8 | 4 | 8 | 16 | 16 |
| 11 | 8 | 4 | 4 | 8 | >16 | 16 | 8 | 8 | 8 | 16 | 16 | 16 |
| 12 | 16 | 4 | 4 | 8 | >16 | 16 | 4 | 8 | 8 | 8 | 16 | 16 |
| 13 | 16 | 4 | 4 | 8 | >16 | 8 | 8 | 8 | 8 | 8 | 16 | 16 |
| 14 | 8 | 4 | 4 | 8 | >16 | 16 | 8 | 8 | 16 | 16 | 16 | 16 |
| 15 | 16 | 4 | 4 | 8 | >16 | 16 | 8 | 8 | 8 | 8 | 16 | 16 |
| 16 | 16 | 8 | 8 | 16 | >16 | 16 | 8 | 8 | 8 | 16 | 16 | 16 |
| 17 | 16 | 8 | 8 | 16 | >16 | 16 | 8 | 8 | 8 | 16 | 16 | 16 |
| 18 | 16 | 8 | 8 | 16 | >16 | 16 | 8 | 16 | 8 | 16 | 16 | 16 |
| 19 | 8 | 4 | 4 | 16 | >16 | 16 | 8 | 8 | 8 | 16 | 16 | 16 |
| 20 | 16 | 4 | 4 | 8 | >16 | 16 | 8 | 8 | 8 | 8 | 16 | 16 |

| # | O | P | Q | R | S | T | U | V | W | X | Y | Ery |
|---|---|---|---|---|---|---|---|---|---|---|---|-----|
| 1 | 8 | 8 | 8 | 16 | 4 | 4 | 8 | 8 | 16 | 8 | 8 | 2 |
| 2 | 16 | 8 | 8 | 16 | 8 | 8 | 8 | 8 | 16 | 8 | 8 | >8 |
| 3 | 8 | 4 | 8 | 8 | 4 | 8 | 8 | 8 | 16 | 8 | 8 | >8 |
| 4 | 8 | 8 | 8 | 16 | 4 | 8 | 8 | 8 | 16 | 8 | 8 | >8 |
| 5 | 8 | 4 | 8 | 8 | 4 | 4 | 4 | 8 | 16 | 8 | 8 | >8 |
| 6 | 16 | 8 | 8 | 8 | 4 | 8 | 8 | 8 | >16 | 8 | 8 | >8 |
| 7 | 8 | 8 | 8 | 8 | 4 | 8 | 8 | 8 | 16 | 8 | 8 | >8 |
| 8 | 16 | 8 | 16 | 16 | 4 | 4 | 8 | 8 | 8 | 8 | 8 | >8 |
| 9 | 8 | 8 | 8 | 16 | 4 | 8 | 16 | >16 | 8 | 16 | 8 | >8 |
| 10 | 16 | 8 | 8 | 16 | 4 | 4 | 4 | 8 | 16 | 8 | 16 | >8 |
| 11 | 8 | 8 | 8 | 16 | 4 | 8 | 8 | 8 | >16 | 8 | 16 | >8 |
| 12 | 16 | 8 | 8 | 16 | 4 | 4 | 8 | 8 | 16 | 8 | 16 | >8 |
| 13 | 8 | 4 | 8 | 16 | 8 | 4 | 8 | 8 | >16 | 8 | 16 | >8 |
| 14 | 8 | 8 | 8 | 16 | 8 | 4 | 16 | >16 | 8 | 8 | 16 | >8 |
| 15 | 8 | 8 | 8 | 16 | 4 | 4 | 16 | 16 | 8 | 16 | 16 | >8 |
| 16 | 8 | 8 | 8 | 16 | 8 | 8 | 16 | >16 | 16 | 16 | 16 | >8 |
| 17 | 8 | 8 | 8 | 16 | 8 | 8 | 8 | >16 | 8 | 16 | 16 | >8 |
| 18 | 16 | 4 | 8 | 16 | 8 | 8 | 8 | >16 | 8 | 8 | >8 | >8 |
| 19 | 8 | 8 | 8 | 8 | 8 | 4 | 8 | 8 | >16 | 8 | 16 | >8 |
| 20 | 8 | 8 | 8 | 8 | 8 | 4 | 8 | 16 | 16 | 8 | 16 | >8 |

TABLE 6-6

MIC against Klebsiella species

| # | A | B | C | D | E, L-M, R | F | G | H | I | J | K | N |
|---|---|---|---|---|-----------|---|---|---|---|---|---|---|
| 28 | 16 | 2 | 2 | 4 | >16 | 16 | 2 | 8 | 8 | 8 | 16 | 16 |
| 29 | 16 | 2 | 2 | 2 | >16 | 16 | 2 | 8 | 4 | 8 | 16 | 16 |
| 30 | 16 | 4 | 2 | 4 | >16 | 8 | 2 | 8 | 8 | 8 | 16 | 16 |
| 31 | 8 | 2 | 2 | 2 | >16 | >16 | 2 | 8 | 4 | 8 | 16 | 16 |
| 32 | 16 | 1 | 1 | 2 | >16 | 16 | 2 | 16 | 4 | 8 | 16 | 16 |
| 33 | 16 | 4 | 2 | 2 | >16 | 8 | 2 | 8 | 4 | 8 | 8 | 8 |
| 34 | 16 | 2 | 2 | 4 | >16 | 8 | 2 | 8 | 4 | 8 | 16 | 16 |
| 35 | 16 | 4 | 2 | 4 | >16 | 8 | 4 | 8 | 4 | 8 | 16 | 16 |
| 36 | 16 | 4 | 2 | 4 | >16 | 16 | 4 | 8 | 4 | 8 | 16 | 16 |
| 37 | 16 | 2 | 2 | 4 | >16 | 16 | 2 | 8 | 4 | 8 | 16 | 16 |
| 38 | 16 | 4 | 2 | 4 | >16 | 8 | 2 | 8 | 8 | 8 | 16 | 8 |
| 39 | 8 | 2 | 2 | 4 | >16 | 8 | 4 | 8 | 8 | 8 | 8 | 8 |
| 40 | 16 | 4 | 2 | 4 | >16 | 8 | 4 | 8 | 8 | 8 | 16 | 16 |
| 41 | 16 | 2 | 2 | 4 | >16 | 8 | 2 | 8 | 8 | 8 | 16 | 16 |
| 42 | 16 | 2 | 2 | 4 | >16 | 8 | 2 | 8 | 4 | 8 | 16 | 8 |
| 43 | 16 | 4 | 2 | 4 | >16 | 8 | 4 | 8 | 4 | 8 | 16 | 8 |
| 44 | >16 | 4 | 2 | 4 | >16 | >16 | 4 | 8 | 8 | 8 | 16 | 16 |
| 45 | 16 | 4 | 2 | 4 | >16 | 8 | 4 | 8 | 8 | 8 | 16 | 16 |
| 46 | 16 | 4 | 2 | 2 | >16 | 8 | 2 | 8 | 4 | 4 | 16 | 8 |
| 47 | 16 | 4 | 2 | 4 | >16 | 16 | 4 | 8 | 8 | 8 | 16 | 16 |

TABLE 6-6-continued

MIC against Klebsiella species

| # | O | P | Q | S | T | U | V | W | X | Y | Ery |
|---|---|---|---|---|---|---|---|---|---|---|-----|
| 28 | 16 | 8 | 16 | 4 | 2 | 8 | 16 | 16 | 8 | 16 | >8 |
| 29 | 8 | 8 | 16 | 4 | 2 | 4 | 8 | 16 | 8 | 16 | >8 |
| 30 | 16 | 16 | 16 | 4 | 2 | 8 | 8 | 16 | 8 | 16 | >8 |
| 31 | 16 | 8 | 16 | 4 | 2 | 4 | 8 | 16 | 8 | 16 | >8 |
| 32 | 16 | 16 | 16 | 2 | 1 | 4 | 8 | 8 | 8 | 16 | >8 |
| 33 | 8 | 8 | 8 | 4 | 4 | 8 | 8 | 16 | 8 | 8 | >8 |
| 34 | 16 | 8 | 16 | 4 | 4 | 8 | 8 | 16 | 8 | 8 | >8 |
| 35 | 16 | 8 | 8 | 4 | 2 | 4 | 8 | 8 | 8 | 8 | >8 |
| 36 | 16 | 16 | 16 | 4 | 4 | 8 | 8 | 16 | 8 | 16 | >8 |
| 37 | 16 | 16 | 16 | 4 | 2 | 4 | 8 | 16 | 8 | 16 | >8 |
| 38 | 16 | 16 | 16 | 4 | 4 | 4 | 8 | 16 | 8 | 8 | >8 |
| 39 | 8 | 8 | 8 | 4 | 2 | 8 | 8 | 8 | 4 | 8 | >8 |
| 40 | 16 | 8 | 16 | 4 | 4 | 8 | 8 | 16 | 4 | 8 | >8 |
| 41 | 16 | 16 | 16 | 2 | 2 | 4 | 8 | 16 | 8 | 16 | >8 |
| 42 | 8 | 16 | 8 | 2 | 2 | 4 | 8 | 8 | 4 | 8 | >8 |
| 43 | 16 | 8 | 8 | 4 | 2 | 4 | 8 | 16 | 8 | 8 | >8 |
| 44 | 16 | >16 | 16 | 4 | 4 | 8 | 8 | 16 | 8 | 16 | >8 |
| 45 | 16 | 16 | 16 | 4 | 4 | 8 | 8 | 8 | 8 | 8 | >8 |
| 46 | 16 | 8 | 16 | 4 | 4 | 8 | 8 | 8 | 8 | 8 | >8 |
| 47 | 16 | 16 | 16 | 8 | 4 | 8 | 8 | 16 | 8 | 8 | >8 |

TABLE 6-7

MIC against *Histophilus somni*

| # | Compounds A-Y | ERY |
|---|---------------|-----|
| 238-240, 243, 246 | ≥16 | >8 |
| 241, 247 | ≥16 | 0.5 |
| 242, 244, 245 | ≥16 | 1 |

TABLE 6-8

MIC against *Mycoplasma bovis*

| # | A | B-F, H-P, X-Y, S-T, V | G | Q | R | U | W | Ery |
|---|---|-----------------------|---|---|---|---|---|-----|
| 248 | 16 | ≥16 | >16 | 4 | 8 | 1 | 0.5 | >8 |
| 249 | 8 | ≥16 | 16 | 4 | 8 | 1 | 1 | >8 |
| 250 | 16 | ≥16 | >16 | 8 | 8 | 4 | 1 | >8 |
| 251 | 16 | ≥16 | >16 | 4 | 8 | 4 | 2 | >8 |
| 252 | 8 | ≥16 | >16 | 2 | 4 | 1 | 0.5 | >8 |
| 253 | 16 | ≥16 | 8 | 4 | 8 | 1 | 0.25 | 4 |
| 254 | 8 | ≥16 | 16 | 8 | 4 | 0.5 | 0.5 | >8 |
| 255 | 16 | ≥16 | 16 | 4 | 8 | 0.25 | 0.25 | >8 |
| 256 | 8 | ≥16 | 16 | 8 | 4 | 2 | 0.5 | >8 |
| 257 | 8 | ≥16 | 8 | 4 | 4 | 2 | 0.25 | >8 |

TABLE 6-9

MIC against *Mannheimia haemolytica*

| # | A, E-F, K, L-N, R, V, X-Y | B-D | G | H | I | J | O | P | Q | S, T | U | Ery |
|---|---|---|---|---|---|---|---|---|---|---|---|---|
| 158 | ≥16 | 1-2 | 4 | 8 | 4 | 8 | 16 | 8 | 16 | 2 | 4 | 4 |
| 159 | ≥16 | 1-2 | 4 | 8 | 4 | 4 | 8 | 16 | 8 | 2 | 4 | >8 |
| 160 | ≥16 | 1-2 | 4 | 8 | 4 | 4 | 16 | 16 | 16 | 2 | 4 | 4 |
| 161 | ≥16 | 1-2 | 2 | 8 | 4 | 4 | 16 | 8 | 16 | 2 | 4 | >8 |
| 162 | ≥16 | 1-2 | 2 | 8 | 4 | ≤0.12 | 16 | 16 | 16 | 4 | 4 | 2 |
| 163 | ≥16 | 1-2 | 2 | 8 | 4 | 8 | 16 | 8 | 8 | 2 | 4 | 4 |
| 164 | ≥16 | 1-2 | 4 | 8 | 4 | 8 | 8 | 8 | 8 | 2 | 4 | >8 |
| 165 | ≥16 | 1-2 | 4 | 8 | 4 | 4 | 8 | 8 | 8 | 2 | 4 | >8 |
| 166 | ≥16 | 1-2 | 2 | 8 | 2 | 4 | 16 | 16 | 16 | 2 | 4 | 1 |
| 167 | ≥16 | 1-2 | 4 | 8 | 4 | 8 | 8 | 8 | 16 | 2 | 4 | 4 |

TABLE 6-10

MIC against *Moraxella bovis*

| # | A | B | C | D | E | F | G | H | I | J | K | L | M |
|---|---|---|---|---|---|---|---|---|---|---|---|---|---|
| 88 | 4 | 0.5 | 0.3 | 0.3 | ≥16 | 2 | 0.3 | 2 | 0.5 | 1 | 4 | 4 | 1 |
| 89 | 8 | 0.5 | 0.3 | 0.3 | ≥16 | 8 | 0.3 | 2 | 1 | 1 | 4 | 8 | 4 |
| 90 | 8 | 0.5 | 0.3 | 0.5 | ≥16 | 4 | 0.5 | 2 | 1 | 2 | 4 | 8 | 4 |
| 91 | 4 | 1 | 0.5 | 0.5 | ≥16 | 8 | 0.5 | 2 | 1 | 2 | 8 | 16 | 4 |
| 92 | 4 | 0.5 | 0.3 | 0.3 | ≥16 | 8 | 0.5 | 2 | 1 | 1 | 4 | 8 | 4 |
| 93 | 8 | 1 | 0.5 | 0.5 | ≥16 | 2 | 0.3 | 2 | 1 | 2 | 4 | 4 | 4 |
| 94 | 8 | 1 | 1 | 0.5 | ≥16 | 8 | 0.5 | 4 | 2 | 2 | 4 | 8 | 4 |
| 95 | 4 | 1 | 0.5 | 0.5 | ≥16 | 2 | 0.5 | 2 | 1 | 2 | 4 | 8 | 4 |
| 96 | 4 | 0.5 | 0.5 | 0.3 | ≥16 | 2 | 0.3 | 2 | 1 | 1 | 4 | 4 | 4 |
| 97 | 8 | 0.5 | 0.5 | 0.5 | ≥16 | 4 | 0.3 | 2 | 1 | 1 | 4 | 8 | 4 |

| # | N | O | P | Q | R | S | T | U | V | W | X | Y | Ery |
|---|---|---|---|---|---|---|---|---|---|---|---|---|---|
| 88 | 1 | 2 | 4 | 4 | 4 | 0.5 | 0.5 | 0.1 | 4 | 2 | 2 | 2 | 0.3 |
| 89 | 4 | 8 | 4 | 4 | 8 | 1 | 0.5 | 2 | 8 | 4 | 2 | 4 | 0.5 |
| 90 | 4 | 8 | 4 | 4 | 8 | 2 | 1 | 2 | 8 | 4 | 4 | 8 | 0.5 |
| 91 | 4 | 8 | 4 | 8 | 8 | 1 | 1 | 2 | 8 | 4 | 4 | 8 | 1 |
| 92 | 4 | 8 | 4 | 8 | 8 | 1 | 1 | 2 | 8 | 4 | 4 | 8 | 0.5 |
| 93 | 2 | 8 | 4 | 4 | 8 | 1 | 1 | 2 | 8 | 2 | 2 | 2 | 0.3 |
| 94 | 4 | 8 | 4 | 4 | 8 | 1 | 1 | 2 | 8 | 4 | 4 | 8 | 0.5 |
| 95 | 4 | 8 | 4 | 4 | 4 | 1 | 1 | 2 | 4 | 2 | 2 | 4 | 0.5 |
| 96 | 2 | 8 | 4 | 4 | 4 | 1 | 1 | 2 | 4 | 2 | 2 | 2 | 0.5 |
| 97 | 4 | 8 | 4 | 8 | 8 | 1 | 1 | 2 | 8 | 2 | 2 | 4 | 0.5 |

TABLE 6-11

MIC against *Proteus mirabilis*

| # | A, E-F, H, J-R, W, Y | B | C | D | G, I | S, X | T | U | V | Ery |
|---|---|---|---|---|---|---|---|---|---|---|
| 48 | >16 | 8 | 8 | 16 | 16 | 16 | 16 | 8 | 16 | >8 |
| 49 | >16 | 8 | 8 | 8 | 16 | 16 | 16 | 8 | 16 | >8 |
| 50 | >16 | 8 | 4 | 8 | 8 | 8 | 8 | 8 | 16 | >8 |
| 51 | >16 | 8 | 4 | 8 | 8 | 16 | 8 | 8 | 16 | >8 |
| 52 | >16 | 8 | 4 | 8 | 8 | 16 | 8 | 8 | 16 | >8 |
| 53 | >16 | 8 | 4 | 8 | 8 | 16 | 8 | 8 | 16 | >8 |
| 54 | >16 | 8 | 8 | 8 | 8 | 16 | 8 | 8 | 16 | >8 |
| 55 | >16 | 8 | 4 | 8 | 8 | 16 | 8 | 8 | 8 | >8 |
| 56 | >16 | 16 | 8 | 16 | 16 | 16 | 16 | 8 | 16 | >8 |
| 57 | >16 | 16 | 8 | 16 | 16 | 16 | 16 | 8 | 16 | >8 |

TABLE 6-12

MIC against *Pasteurella multocida*

| # | A | B | C | D | E | F | G | H | I | J | K | L | M |
|---|---|---|---|---|---|---|---|---|---|---|---|---|---|
| 168 | 8 | 1 | 1 | 1 | >16 | 8 | 1 | 4 | 2 | 2 | 8 | 8 | 8 |
| 169 | 8 | 2 | 2 | 4 | >16 | 8 | 4 | 8 | 2 | 4 | 2 | 8 | 4 |
| 170 | 8 | 4 | 2 | 8 | >16 | 16 | 4 | 8 | 2 | 4 | 2 | 8 | 2 |
| 171 | 8 | 1 | 1 | 2 | >16 | 8 | 2 | 4 | 2 | 4 | 8 | >16 | 8 |
| 172 | 8 | 4 | 2 | 4 | >16 | 8 | 2 | 8 | 2 | 4 | 2 | 16 | 2 |
| 173 | 16 | 8 | 8 | 16 | >16 | 16 | 8 | 8 | 2 | 4 | 2 | 16 | 2 |
| 174 | 4 | 1 | 1 | 0.5 | 8 | 2 | 1 | 4 | 1 | 1 | 4 | 8 | 4 |
| 175 | 8 | 2 | 2 | 4 | >16 | 8 | 2 | 8 | 2 | 4 | 2 | 8 | 2 |
| 176 | 8 | 4 | 4 | 4 | >16 | 8 | 2 | 8 | 2 | 4 | 2 | 8 | 2 |
| 177 | 16 | 4 | 4 | 8 | >16 | 16 | 8 | 8 | 2 | 8 | 2 | >16 | 4 |
| 178 | 8 | 4 | 4 | 8 | >16 | >16 | 8 | 16 | 2 | 8 | 2 | >16 | 2 |
| 179 | 16 | 4 | 4 | 8 | >16 | >16 | 8 | 8 | 2 | 4 | 2 | 8 | 2 |
| 180 | 8 | 4 | 4 | 8 | >16 | >16 | 4 | 8 | 2 | 4 | 2 | 8 | 2 |
| 181 | 8 | 4 | 4 | 8 | >16 | >16 | 8 | 8 | 2 | 4 | ≤0.12 | 8 | 2 |
| 182 | 8 | 4 | 4 | 8 | >16 | >16 | 8 | 16 | 2 | 8 | 2 | >16 | 2 |
| 183 | 8 | 4 | 8 | 16 | >16 | >16 | 16 | 16 | 4 | 8 | 2 | >16 | 4 |
| 184 | 16 | 4 | 4 | 8 | >16 | 16 | 8 | 8 | 2 | 4 | 1 | 8 | 2 |
| 185 | 8 | 4 | 4 | 8 | >16 | >16 | 8 | 8 | 2 | 4 | 2 | 16 | 2 |
| 186 | 16 | 4 | 4 | 8 | >16 | >16 | 8 | 16 | 2 | 4 | 2 | 16 | 2 |
| 187 | 8 | 1 | 1 | 1 | >16 | 16 | 1 | 4 | 1 | 2 | 1 | 8 | 1 |

| # | N | O | P | Q | R | S | T | U | V | W | X | Y | Ery |
|---|---|---|---|---|---|---|---|---|---|---|---|---|---|
| 168 | 4 | 16 | 8 | 8 | 16 | 2 | 2 | 4 | 8 | 4 | 4 | 8 | 0.5 |
| 169 | 4 | 16 | 16 | 16 | 16 | 4 | 4 | 4 | 8 | 16 | 4 | 8 | 1 |
| 170 | 4 | 16 | 16 | 16 | 16 | 4 | 4 | 4 | 8 | >16 | 8 | 8 | 1 |

TABLE 6-12-continued

MIC against *Pasteurella multocida*

| 171 | 4 | 8 | 8 | 8 | 16 | 2 | 2 | 2 | 8 | 4 | 4 | 8 | 0.5 |
|---|---|---|---|---|---|---|---|---|---|---|---|---|---|
| 172 | 4 | 8 | 16 | 8 | 16 | 4 | 4 | 4 | 8 | >16 | 8 | 8 | 1 |
| 173 | 4 | 16 | 16 | 16 | 16 | 8 | 8 | 8 | 8 | >16 | 8 | >16 | 2 |
| 174 | 2 | 8 | 4 | 4 | 8 | 1 | 1 | 4 | 4 | 4 | 4 | 2 | 8 |
| 175 | 4 | 8 | 16 | 8 | 16 | 4 | 4 | 4 | 8 | 16 | 4 | 8 | 1 |
| 176 | 4 | 8 | 16 | 8 | 16 | 4 | 4 | 4 | 8 | 8 | 4 | 8 | 0.5 |
| 177 | 4 | 16 | 16 | 16 | 16 | 8 | 4 | 4 | 8 | >16 | 4 | >16 | 2 |
| 178 | 8 | 16 | 8 | 16 | 16 | 8 | 4 | 4 | 8 | >16 | 8 | >16 | 4 |
| 179 | 4 | 16 | 16 | 16 | 16 | 8 | 4 | 4 | 8 | >16 | 8 | >16 | 2 |
| 180 | 4 | 16 | 16 | 16 | 16 | 8 | 4 | 4 | 8 | >16 | 8 | 16 | 2 |
| 181 | 4 | 16 | 16 | 16 | 16 | 8 | 4 | 4 | 8 | >16 | 8 | 16 | 2 |
| 182 | 4 | 16 | 16 | 16 | 16 | 8 | 4 | 4 | 8 | >16 | 8 | >16 | 2 |
| 183 | 4 | 16 | 16 | 16 | 16 | 8 | 8 | 4 | 8 | >16 | 8 | >16 | >8 |
| 184 | 4 | 16 | 16 | 16 | 16 | 8 | 4 | 8 | 8 | 8 | 8 | 16 | 2 |
| 185 | 4 | 16 | 16 | 16 | 16 | 8 | 4 | 4 | 8 | 16 | 8 | 8 | >8 |
| 186 | 4 | 16 | 16 | 16 | 16 | 8 | 4 | 4 | 8 | 16 | 8 | 16 | 2 |
| 187 | 4 | 8 | 4 | 4 | 8 | 2 | 2 | 2 | 8 | 8 | 4 | 8 | >8 |

TABLE 6-13

MIC against *Pseudomonas aeruginosa*

| # | A, K, M-N, P-R, V, W, Y | B | C | D | E, L, O | F | G | H | I | J | S | T | U | X | Ery |
|---|---|---|---|---|---|---|---|---|---|---|---|---|---|---|---|
| 58 | >16 | 8 | 8 | >16 | ≥16 | 16 | >16 | >16 | >16 | >16 | 16 | 16 | >16 | 16 | >8 |
| 59 | 8 | 2 | 1 | 2 | ≥16 | 8 | 2 | 4 | 1 | 2 | 4 | 4 | 4 | 4 | >8 |
| 60 | >16 | 8 | 16 | >16 | ≥16 | 8 | >16 | 16 | >16 | >16 | 16 | 16 | 16 | 16 | >8 |
| 61 | >16 | 8 | 16 | >16 | ≥16 | 8 | >16 | 16 | >16 | >16 | 16 | 16 | 16 | 16 | >8 |
| 62 | >16 | 4 | 8 | 16 | ≥16 | 8 | >16 | 16 | >16 | >16 | 8 | 8 | 16 | 16 | >8 |
| 63 | >16 | 4 | 8 | >16 | ≥16 | 8 | >16 | 16 | >16 | >16 | 16 | 8 | 16 | 8 | >8 |
| 64 | >16 | 8 | 8 | >16 | ≥16 | 8 | >16 | 16 | >16 | >16 | 8 | 8 | 16 | 16 | >8 |
| 65 | >16 | 8 | 16 | >16 | ≥16 | 16 | >16 | 16 | >16 | 4 | 16 | 16 | >16 | 16 | >8 |
| 66 | >16 | 4 | 8 | >16 | ≥16 | 8 | >16 | 16 | >16 | >16 | 8 | 8 | 16 | 8 | >8 |
| 67 | >16 | 8 | 16 | >16 | ≥16 | 8 | >16 | 16 | >16 | >16 | 16 | 8 | >16 | 16 | >8 |

TABLE 6-14

MIC against *Staphylococcus aureus* including MRSA

| # | A, E, P-R | B | C | D | F | G | H | I | J | K | L |
|---|---|---|---|---|---|---|---|---|---|---|---|
| 98 | ≥16 | 4 | 2 | 4 | 16 | 4 | 4 | 4 | 8 | 4 | 16 |
| 99 | ≥16 | 4 | 2 | 2 | 8 | 4 | 4 | 4 | 4 | 4 | 16 |
| 100 | ≥16 | 4 | 2 | 2 | 8 | 2 | 4 | 2 | 4 | 4 | 16 |
| 101 | ≥16 | 2 | 2 | 2 | 8 | 2 | 4 | 2 | 4 | 4 | >16 |
| 102 | ≥16 | 4 | 1 | 2 | 8 | 2 | 4 | 4 | 4 | 4 | 16 |
| 103 | ≥16 | 4 | 2 | 2 | 16 | 4 | 4 | 2 | 4 | 4 | 16 |
| 104 | ≥16 | 4 | 2 | 2 | 8 | 4 | 4 | 4 | 4 | 8 | 16 |
| 105 | ≥16 | 2 | 1 | 1 | 8 | 1 | 4 | 2 | 4 | 4 | 16 |
| 106 | ≥16 | 2 | 2 | 2 | 8 | 2 | 4 | 4 | 4 | 4 | >16 |
| 107 | ≥16 | 2 | 1 | 1 | 16 | 2 | 4 | 2 | 4 | 4 | 16 |
| 108 | ≥16 | 4 | 2 | 2 | 8 | 2 | 4 | 4 | 4 | 4 | 8 |
| 109 | ≥16 | 2 | 1 | 1 | 8 | 2 | 4 | 2 | 4 | 4 | 16 |
| 110 | ≥16 | 2 | 1 | 2 | 8 | 2 | 4 | 2 | 4 | 4 | 8 |
| 111 | ≥16 | 4 | 2 | 2 | 16 | 4 | 8 | 4 | 4 | 4 | >16 |
| 112 | ≥16 | 2 | 1 | 2 | 8 | 2 | 4 | 2 | 4 | 2 | 8 |
| 113 | ≥16 | 1 | 0.5 | 1 | 8 | 0.5 | 4 | 1 | 2 | 4 | 8 |
| 114 | ≥16 | 2 | 1 | 2 | 8 | 2 | 4 | 2 | 4 | 4 | 16 |
| 115 | ≥16 | 2 | 1 | 2 | 8 | 2 | 4 | 2 | 4 | 8 | 16 |
| 116 | ≥16 | 2 | 1 | 1 | 8 | 1 | 4 | 2 | 2 | 4 | 8 |
| 117 | ≥16 | 2 | 1 | 2 | 16 | 2 | 4 | 2 | 4 | 4 | 8 |
| 118 | ≥16 | 4 | 1 | 2 | 8 | 2 | 4 | 2 | 2 | 2 | 16 |
| 119 | ≥16 | 4 | 2 | 4 | 8 | 4 | 4 | 2 | 4 | 4 | >16 |
| 120 | ≥16 | 2 | 1 | 1 | 8 | 1 | 4 | 2 | 2 | 4 | 8 |
| 121 | ≥16 | 4 | 2 | 4 | 8 | 4 | 4 | 2 | 4 | 4 | 16 |
| 122 | ≥16 | 2 | 1 | 1 | 8 | 1 | 4 | 2 | 2 | 4 | 8 |
| 123 | ≥16 | 2 | 1 | 2 | 16 | 2 | 4 | 4 | 4 | 4 | 16 |
| 124 | ≥16 | 2 | 2 | 2 | 8 | 4 | 4 | 2 | 4 | 4 | 16 |
| 125 | ≥16 | 2 | 1 | 2 | 8 | 2 | 4 | 2 | 4 | 4 | >16 |
| 126 | ≥16 | 2 | 2 | 4 | 8 | 4 | 8 | 2 | 4 | 4 | >16 |
| 127 | ≥16 | 2 | 2 | 4 | 16 | 4 | 8 | 4 | 4 | 4 | >16 |

| # | M | N | O | S | T | U | V | W | X | Y | Ery |
|---|---|---|---|---|---|---|---|---|---|---|---|
| 98 | 8 | 4 | 8 | 4 | 4 | 8 | 4 | 8 | 8 | 8 | 0.25 |
| 99 | 4 | 4 | 8 | 4 | 4 | 8 | 4 | 8 | 8 | 8 | 0.25 |
| 100 | 8 | 4 | 8 | 4 | 4 | 8 | 4 | 8 | 8 | 8 | 0.25 |
| 101 | 8 | 4 | 16 | 4 | 4 | 8 | 4 | 8 | 8 | 8 | 0.25 |
| 102 | 8 | 4 | 8 | 4 | 4 | 8 | 4 | 8 | 8 | 8 | 0.25 |
| 103 | 8 | 4 | 16 | 4 | 2 | 4 | 4 | 8 | 8 | 8 | 0.25 |
| 104 | 8 | 4 | 8 | 4 | 4 | 8 | 4 | 8 | 8 | 8 | 0.25 |
| 105 | 8 | 4 | 16 | 2 | 2 | 8 | 4 | 8 | 8 | 8 | 0.25 |
| 106 | 8 | 4 | 16 | 4 | 4 | 8 | 4 | 8 | 8 | 8 | 0.25 |
| 107 | 8 | 4 | 16 | 4 | 2 | 8 | 4 | 8 | 8 | 8 | 0.25 |
| 108 | 4 | 4 | 8 | 4 | 2 | 8 | 4 | 8 | 8 | 4 | >8 |
| 109 | 4 | 4 | 8 | 2 | 2 | 8 | 4 | 4 | 8 | 4 | 1 |
| 110 | 8 | 4 | 8 | 4 | 2 | 8 | 4 | 8 | 8 | 4 | >8 |
| 111 | 8 | 4 | 8 | 4 | 4 | 8 | 4 | 8 | 8 | 4 | >8 |
| 112 | 4 | 2 | 8 | 4 | 4 | 8 | 4 | 8 | 8 | 4 | 0.5 |
| 113 | 4 | 4 | 8 | 2 | 4 | 8 | 4 | 4 | 8 | 8 | >8 |
| 114 | 4 | 4 | 8 | 4 | 2 | 8 | 4 | 8 | 8 | 4 | >8 |
| 115 | 4 | 4 | 8 | 4 | 4 | 8 | 4 | 8 | 8 | 4 | >8 |
| 116 | 4 | 4 | 8 | 4 | 4 | 8 | 4 | 8 | 8 | 8 | >8 |
| 117 | 4 | 4 | 8 | 4 | 4 | 8 | 4 | 8 | 8 | 4 | >8 |
| 118 | 4 | 4 | 16 | 4 | 2 | 8 | 4 | 8 | 8 | 4 | >8 |
| 119 | 4 | 4 | 8 | 4 | 4 | 8 | 4 | 8 | 8 | 8 | >8 |
| 120 | 4 | 4 | 8 | 2 | 2 | 8 | 4 | 8 | 8 | 4 | >8 |

TABLE 6-14-continued

MIC against *Staphylococcus aureus* including MRSA

| # | A, E, P-R | B | C | D | F | G | H | I | J | K | L |
|---|---|---|---|---|---|---|---|---|---|---|---|
| 121 | 4 | 4 | 16 | 4 | 2 | 8 | 4 | 8 | 8 | 4 | >8 |
| 122 | 4 | 4 | 8 | 2 | 1 | 8 | 4 | 8 | 8 | 4 | >8 |
| 123 | 4 | 4 | 8 | 4 | 2 | 8 | 4 | 8 | 8 | 8 | >8 |
| 124 | 4 | 4 | 16 | 4 | 4 | 8 | 4 | 8 | 8 | 4 | >8 |
| 125 | 8 | 4 | >16 | 4 | 4 | 8 | 4 | 8 | 8 | 4 | >8 |
| 126 | 8 | 4 | 16 | 4 | 4 | 8 | 4 | 8 | 8 | 8 | >8 |
| 127 | 8 | 4 | 8 | 4 | 4 | 8 | 4 | 8 | 8 | 8 | >8 |

TABLE 6-15

MIC against *Streptococcus agalactiae*

| # | A | B | C | D | E, L | F | G | H | I | J | K | M | Ery |
|---|---|---|---|---|---|---|---|---|---|---|---|---|---|
| 188 | 8 | 0.5 | 1 | 2 | ≥16 | >16 | 2 | 2 | 2 | 1 | 4 | 8 | 0.03 |
| 189 | 16 | 0.5 | 2 | 2 | ≥16 | >16 | 2 | 4 | 2 | 2 | 8 | 8 | 0.06 |
| 190 | 4 | 0.5 | 0.5 | 1 | ≥16 | >16 | 2 | 2 | 2 | 2 | 4 | 4 | 0.03 |
| 191 | 8 | 0.5 | 1 | 4 | ≥16 | >16 | 4 | 8 | 4 | 2 | 16 | >16 | 0.03 |
| 192 | 8 | 1 | 1 | 2 | ≥16 | >16 | 2 | 16 | 8 | 4 | 16 | 16 | 0.06 |
| 193 | 4 | 0.5 | 0.5 | 2 | ≥16 | 8 | 2 | 2 | 2 | 1 | 8 | 8 | 0.06 |
| 194 | 8 | 0.5 | 1 | 2 | ≥16 | >16 | 2 | 4 | 2 | 2 | 4 | 8 | 0.03 |
| 195 | 4 | 0.25 | 0.5 | 2 | ≥16 | >16 | 4 | 1 | 2 | 2 | 2 | 4 | 0.03 |
| 196 | 4 | 0.25 | 0.5 | 1 | ≥16 | >16 | 2 | 2 | 2 | 1 | 4 | 4 | 0.03 |
| 197 | 8 | 1 | 2 | 4 | ≥16 | >16 | 4 | 8 | 8 | 4 | 8 | >16 | 0.03 |

| # | N | O | P | Q | R | S | T | U | V | W | X | Y | Ery |
|---|---|---|---|---|---|---|---|---|---|---|---|---|---|
| 188 | 8 | 8 | 8 | 8 | 8 | 1 | 1 | 0.5 | 4 | 8 | 4 | 8 | 0.03 |
| 189 | 16 | 4 | 8 | 8 | 8 | 1 | 1 | 0.5 | 4 | 8 | 4 | 16 | 0.06 |
| 190 | 8 | 8 | 8 | 4 | 8 | 1 | 0.5 | 1 | 4 | 8 | 4 | 8 | 0.03 |
| 191 | >16 | 8 | 16 | 8 | 8 | 2 | 1 | 2 | 8 | 8 | 2 | >16 | 0.03 |
| 192 | 8 | 8 | 16 | 4 | 8 | 2 | 1 | 4 | 8 | 8 | 8 | >16 | 0.06 |
| 193 | 8 | 8 | 8 | 4 | 8 | 1 | 1 | 1 | 8 | 8 | 2 | 8 | 0.06 |
| 194 | 8 | 8 | 8 | 4 | 8 | 0.5 | 1 | 0.5 | 4 | 8 | 4 | 16 | 0.03 |
| 195 | 8 | 4 | 8 | 4 | 8 | 0.5 | 0.5 | 1 | 4 | 8 | 4 | 16 | 0.03 |
| 196 | 8 | 8 | 8 | 8 | 8 | 1 | 1 | 1 | 2 | 8 | 2 | 8 | 0.03 |
| 197 | 16 | 4 | 16 | 4 | 8 | 1 | 2 | 2 | 8 | 8 | 8 | >16 | 0.03 |

TABLE 6-16

MIC against *Staphylococcus pseudintermedius* (+ MSRP)

| # | A | B | C | D | E | F | G | H | I | J | K | L | M |
|---|---|---|---|---|---|---|---|---|---|---|---|---|---|
| 128 | 8 | 1 | 1 | 2 | 8 | 2 | 2 | 2 | 2 | 4 | 4 | 8 | 8 |
| 129 | 8 | 2 | 1 | 2 | 16 | 2 | 2 | 4 | 2 | 4 | 4 | 16 | 8 |
| 130 | 8 | 1 | 1 | 2 | 8 | 2 | 1 | 2 | 1 | 2 | 4 | 8 | 8 |
| 131 | 8 | 1 | 1 | 2 | 16 | 2 | 2 | 4 | 2 | 2 | 4 | 8 | 8 |
| 132 | 8 | 1 | 1 | 2 | 16 | 4 | 2 | 4 | 2 | 2 | 4 | 16 | 8 |
| 133 | 8 | 1 | 1 | 1 | 8 | 2 | 1 | 2 | 2 | 2 | 4 | 8 | 8 |
| 134 | 8 | 1 | 1 | 2 | 8 | 2 | 1 | 2 | 2 | 2 | 4 | 16 | 8 |
| 135 | 4 | 1 | 1 | 2 | 8 | 2 | 2 | 2 | 2 | 4 | 4 | 16 | 16 |
| 136 | 8 | 1 | 1 | 2 | 16 | 2 | 2 | 2 | 2 | 2 | 4 | 16 | 8 |
| 137 | 4 | 1 | 1 | 2 | 16 | 2 | 2 | 2 | 2 | 2 | 4 | 16 | 8 |
| 138 | 8 | 2 | 1 | 2 | >16 | 4 | 2 | 4 | 1 | 2 | 4 | 8 | 4 |
| 139 | 8 | 2 | 1 | 2 | 16 | 2 | 1 | 4 | 2 | 4 | 4 | 8 | 8 |
| 140 | 8 | 2 | 2 | 2 | >16 | 4 | 2 | 4 | 2 | 4 | 4 | 16 | 8 |
| 141 | 8 | 2 | 2 | 2 | 16 | 2 | 2 | 4 | 2 | 4 | 4 | 16 | 8 |
| 142 | 8 | 1 | 1 | 1 | 8 | 4 | 1 | 4 | 1 | 2 | 4 | 4 | 4 |
| 143 | 8 | 2 | 2 | 4 | >16 | 4 | 2 | 4 | 2 | 4 | 8 | 16 | 8 |
| 144 | 8 | 2 | 2 | 2 | 16 | 4 | 2 | 4 | 2 | 4 | 4 | 16 | 8 |
| 145 | 8 | 2 | 2 | 2 | 16 | 4 | 2 | 4 | 2 | 4 | 4 | 8 | 8 |
| 146 | 8 | 2 | 1 | 2 | >16 | 4 | 2 | 4 | 2 | 4 | 4 | 16 | 8 |
| 147 | 8 | 2 | 1 | 2 | >16 | 2 | 2 | 4 | 2 | 4 | 4 | 8 | 8 |

| # | N | O | P | Q | R | S | T | U | V | W | X | Y | Ery |
|---|---|---|---|---|---|---|---|---|---|---|---|---|---|
| 128 | 4 | 4 | 8 | 8 | 8 | 2 | 2 | 2 | 4 | 8 | 4 | 2 | 0.25 |
| 129 | 4 | 8 | 8 | 8 | 8 | 2 | 2 | 4 | 4 | 8 | 4 | 2 | 0.25 |
| 130 | 4 | 4 | 8 | 8 | 8 | 2 | 2 | 8 | 4 | 4 | 2 | 0.25 |
| 131 | 4 | 8 | 8 | 8 | 8 | 2 | 2 | 4 | 4 | 8 | 4 | 2 | 0.25 |
| 132 | 4 | 8 | 8 | 8 | 8 | 2 | 2 | 4 | 8 | 4 | 4 | 0.25 |
| 133 | 4 | 8 | 8 | 8 | 8 | 2 | 2 | 2 | 2 | 4 | 2 | 1 | 0.25 |
| 134 | 4 | 8 | 8 | 8 | 8 | 2 | 2 | 4 | 4 | 4 | 4 | 1 | 0.25 |
| 135 | 4 | 8 | 8 | 8 | 8 | 2 | 2 | 4 | 4 | 8 | 4 | 2 | 0.12 |
| 136 | 4 | 8 | 8 | 8 | 8 | 2 | 2 | 4 | 4 | 8 | 4 | 2 | 0.25 |
| 137 | 4 | 4 | 8 | 8 | 8 | 2 | 2 | 4 | 4 | 4 | 4 | 1 | 0.12 |
| 138 | 4 | 8 | 16 | 16 | 8 | 4 | 2 | 16 | 4 | 4 | 4 | 2 | >8 |
| 139 | 4 | 8 | 8 | 8 | 8 | 2 | 2 | 4 | 2 | 4 | 2 | 2 | 0.25 |
| 140 | 4 | 8 | 8 | 8 | 8 | 2 | 2 | 4 | 4 | 4 | 4 | 2 | >8 |
| 141 | 4 | 8 | 8 | 8 | 8 | 2 | 2 | 4 | 4 | 4 | 4 | 2 | >8 |
| 142 | 4 | 8 | 4 | 8 | 8 | 1 | 1 | 4 | 2 | 4 | 2 | 2 | >8 |
| 143 | 4 | 4 | 8 | 8 | 8 | 2 | 2 | 4 | 4 | 8 | 4 | 2 | >8 |
| 144 | 4 | 4 | 8 | 8 | 8 | 2 | 2 | 4 | 4 | 4 | 4 | 1 | >8 |
| 145 | 4 | 8 | 8 | 8 | 8 | 2 | 2 | 4 | 4 | 4 | 4 | 2 | >8 |
| 146 | 4 | 8 | 8 | 8 | 8 | 2 | 2 | 4 | 4 | 4 | 4 | 2 | >8 |
| 147 | 4 | 4 | 8 | 8 | 8 | 2 | 2 | 4 | 4 | 4 | 4 | 2 | >8 |

TABLE 6-17

MIC against *Serratia marcescens*

| # | A, E, F, H, J-R, Y | B | C | D | G | I | S | T | U | V | W | X | Ery |
|---|---|---|---|---|---|---|---|---|---|---|---|---|---|
| 68 | ≥16 | 4 | 4 | 8 | 8 | 8 | 4 | 4 | 8 | 8 | 16 | 16 | >8 |
| 69 | ≥16 | 4 | 4 | 8 | 16 | 4 | 4 | 8 | 8 | 16 | 8 | >8 |
| 70 | ≥16 | 8 | 8 | 8 | 4 | 16 | 4 | 4 | 8 | 16 | 16 | >16 | >8 |
| 71 | ≥16 | 2 | 4 | 8 | 4 | 16 | 4 | 4 | 8 | 16 | 16 | 16 | >8 |
| 72 | ≥16 | 4 | 4 | 8 | 8 | 16 | 8 | 4 | 8 | 16 | 16 | 16 | >8 |
| 73 | ≥16 | 2 | 2 | 4 | 8 | 4 | 4 | 8 | 8 | 8 | 16 | >8 |
| 74 | ≥16 | 4 | 4 | 8 | 4 | 8 | 4 | 8 | 16 | 16 | 16 | >8 |
| 75 | ≥16 | 4 | 4 | 8 | 8 | 16 | 8 | 4 | 8 | 16 | 16 | 16 | >8 |
| 76 | ≥16 | 4 | 4 | 8 | 8 | 8 | 4 | 8 | 8 | 16 | 16 | 16 | >8 |
| 77 | ≥16 | 4 | 2 | 4 | 4 | 16 | 4 | 4 | 8 | 16 | 16 | 16 | >8 |

TABLE 6-18

MIC against *Streptococcus canis*

| # | A | B | C | D | E | F | G | H | I | J | K | L | M |
|---|---|---|---|---|---|---|---|---|---|---|---|---|---|
| 198 | 8 | 0.5 | 0.5 | 1 | >16 | 8 | 2 | 4 | 4 | 2 | 8 | >16 | 8 |
| 199 | 4 | 0.5 | 1 | 1 | >16 | >16 | 2 | 4 | 2 | 1 | 16 | >16 | 8 |
| 200 | 4 | 0.25 | 0.25 | 0.5 | >16 | 16 | 2 | 4 | 2 | 2 | 8 | >16 | 8 |
| 201 | 4 | 0.25 | 0.5 | 1 | >16 | 16 | 2 | 4 | 4 | 2 | 8 | >16 | 8 |
| 202 | 4 | 0.5 | 0.5 | 1 | >16 | 8 | 2 | 4 | 2 | 2 | 8 | 16 | 4 |
| 203 | 4 | 0.5 | 0.5 | 2 | >16 | 8 | 2 | 4 | 2 | 2 | 8 | >16 | 8 |
| 204 | 8 | 0.25 | 0.5 | 1 | >16 | 16 | 2 | 4 | 2 | 2 | 8 | >16 | 8 |
| 205 | 8 | 0.5 | 0.5 | 1 | >16 | 4 | 1 | 4 | 4 | 2 | 8 | >16 | 8 |
| 206 | 8 | 0.25 | 1 | 1 | >16 | 8 | 2 | 4 | 4 | 4 | 8 | 16 | 4 |
| 207 | 8 | 0.25 | 1 | 1 | >16 | >16 | 2 | 8 | 4 | 2 | 8 | >16 | 8 |

| # | N | O | P | Q | R | S | T | U | V | W | X | Y | Ery |
|---|---|---|---|---|---|---|---|---|---|---|---|---|---|
| 198 | 4 | 8 | 4 | 8 | 8 | 1 | 0.5 | 1 | 4 | 4 | 4 | 8 | 0.06 |
| 199 | 8 | 8 | 8 | 4 | 8 | 1 | 0.5 | 1 | 8 | 8 | 4 | 16 | 0.06 |
| 200 | 8 | 8 | 8 | 4 | 8 | 0.5 | 0.25 | 0.5 | 8 | 4 | 4 | 8 | 0.12 |
| 201 | 4 | 8 | 8 | 4 | 8 | 0.5 | 0.5 | 1 | 8 | 4 | 8 | 16 | 0.06 |
| 202 | 4 | 4 | 4 | 4 | 4 | 0.5 | 0.5 | 1 | 4 | 4 | 4 | 8 | 0.06 |
| 203 | 8 | 8 | 8 | 4 | 8 | 0.5 | 0.5 | 1 | 8 | 4 | 4 | 8 | 0.06 |
| 204 | 8 | 8 | 8 | 8 | 8 | 1 | 0.5 | 1 | 8 | 4 | 4 | 8 | 0.06 |
| 205 | 4 | 8 | 8 | 4 | 8 | 0.5 | 0.5 | 1 | 8 | 4 | 4 | 8 | 0.06 |
| 206 | 4 | 4 | 8 | 4 | 8 | 1 | 0.5 | 1 | 8 | 4 | 4 | 8 | 0.06 |
| 207 | 8 | 4 | 8 | 4 | 8 | 1 | 0.5 | 1 | 8 | 4 | 4 | 16 | 0.06 |

TABLE 6-19

MIC against coagulase negative *Staphylococcus species*

| # | A | B | C | D | E | F | G | H | I | J | K | L | M |
|---|---|---|---|---|---|---|---|---|---|---|---|---|---|
| 148 | 8 | 0.5 | 0.25 | ≤0.12 | 8 | 2 | ≤0.12 | 2 | 0.5 | 1 | 2 | 2 | 2 |
| 149 | 8 | 1 | 0.5 | 0.5 | 8 | 2 | 1 | 2 | 1 | 1 | 2 | 8 | 4 |
| 150 | 8 | 0.5 | 0.5 | 0.5 | 8 | 2 | 0.5 | 2 | 1 | 2 | 2 | 8 | 4 |
| 151 | 16 | 2 | 1 | 2 | >16 | 8 | 2 | 4 | 2 | 4 | 4 | 8 | 8 |
| 152 | 8 | 2 | 1 | 1 | >16 | 4 | 1 | 2 | 1 | 2 | 2 | 8 | 4 |
| 153 | 8 | 1 | 0.5 | 0.5 | 16 | 1 | 0.5 | 2 | 0.5 | 1 | 2 | 8 | 2 |
| 154 | 16 | 2 | 1 | 1 | >16 | 4 | 2 | 4 | 2 | 4 | 4 | >16 | 8 |
| 155 | 16 | 2 | 2 | 2 | >16 | 8 | 4 | 4 | 4 | 4 | 4 | 16 | 4 |
| 156 | 8 | 1 | 1 | 2 | 16 | 4 | 2 | 2 | 2 | 2 | 2 | 16 | 4 |
| 157 | 4 | 0.25 | ≤0.12 | ≤0.12 | 8 | 1 | ≤0.12 | 2 | 0.25 | 0.5 | 0.5 | 2 | 2 |

| # | N | O | P | Q | R | S | T | U | V | W | X | Y | Ery |
|---|---|---|---|---|---|---|---|---|---|---|---|---|---|
| 148 | 2 | 4 | 4 | 4 | 8 | 0.5 | 0.5 | 4 | 4 | 2 | 2 | 2 | 0.12 |
| 149 | 2 | 4 | 8 | 8 | 8 | 1 | 1 | 4 | 2 | 4 | 2 | 2 | 0.12 |
| 150 | 2 | 8 | 16 | 8 | 16 | 2 | 1 | 4 | 2 | 2 | 2 | 1 | 0.25 |
| 151 | 4 | 8 | 16 | 16 | 16 | 4 | 4 | 8 | 4 | 8 | 8 | 4 | 0.25 |
| 152 | 2 | 8 | 8 | 8 | 8 | 2 | 2 | 4 | 2 | 4 | 4 | 2 | 0.25 |
| 153 | 2 | 8 | 16 | 8 | 8 | 1 | 1 | 2 | 2 | 4 | 2 | 2 | 0.5 |
| 154 | 4 | 8 | 16 | 8 | 16 | 2 | 2 | 4 | 4 | 4 | 4 | 4 | 0.5 |
| 155 | 4 | 8 | >16 | 16 | 8 | 4 | 2 | 8 | 4 | 8 | 8 | 4 | 0.25 |
| 156 | 4 | 8 | 8 | 8 | 8 | 1 | 1 | 4 | 4 | 4 | 4 | 2 | 0.25 |
| 157 | 1 | 4 | 4 | 4 | 8 | 0.5 | 0.5 | 2 | 2 | 2 | 2 | 2 | 0.12 |

TABLE 6-20

MIC against *Streptococcus uberis*

| # | A | B | C | D | E | F | G | H | I | J | K | L | M |
|---|---|---|---|---|---|---|---|---|---|---|---|---|---|
| 218 | 8 | 0.5 | 1 | 2 | >16 | >16 | 2 | 4 | 2 | 2 | 4 | 16 | 4 |
| 219 | 4 | 0.25 | 1 | 2 | >16 | 16 | 4 | 2 | 2 | 1 | 4 | 8 | 4 |
| 220 | 8 | 0.25 | 0.5 | 1 | >16 | >16 | 1 | 2 | 1 | 1 | 4 | 8 | 4 |
| 221 | 4 | 0.25 | ≤0.12 | 0.25 | >16 | 4 | 0.5 | 2 | 1 | 1 | 2 | 4 | 1 |
| 222 | 4 | 0.25 | 1 | 1 | >16 | 16 | 1 | 2 | 1 | 1 | 4 | 8 | 4 |
| 223 | 4 | 0.5 | 0.5 | 0.5 | >16 | >16 | 4 | 2 | 1 | 1 | 4 | 8 | 4 |
| 224 | 4 | ≤0.12 | 0.5 | 1 | >16 | >16 | 1 | 2 | 1 | 1 | 4 | 16 | 4 |
| 225 | 2 | ≤0.12 | 1 | 0.25 | >16 | 8 | 0.5 | 1 | 1 | 0.5 | 4 | 8 | 4 |
| 226 | 2 | ≤0.12 | 0.5 | 0.5 | >16 | >16 | 1 | 2 | 1 | 1 | 4 | 8 | 2 |

TABLE 6-20-continued

MIC against *Streptococcus uberis*

| | | | | | | | | | | | | |
|---|---|---|---|---|---|---|---|---|---|---|---|---|
| 227 | 2 | ≤0.12 | ≤0.12 | 0.5 | >16 | 4 | 0.5 | 1 | 0.5 | 0.5 | 2 | 8 | 1 |

| # | N | O | P | Q | R | S | T | U | V | W | X | Y | Ery |
|---|---|---|---|---|---|---|---|---|---|---|---|---|-----|
| 218 | 8 | 8 | 8 | 8 | 8 | 1 | 0.5 | 0.5 | 4 | 8 | 2 | 16 | 0.06 |
| 219 | 4 | 8 | 8 | 8 | 8 | 1 | 0.5 | 1 | 4 | 4 | 2 | 16 | 0.5 |
| 220 | 4 | 4 | 4 | 4 | 4 | 0.5 | 0.25 | 0.25 | 4 | 4 | 1 | 16 | 0.06 |
| 221 | 2 | 4 | 1 | 4 | 2 | 0.25 | ≤0.12 | 0.25 | 4 | 2 | 4 | 8 | 1 |
| 222 | 2 | 4 | 4 | 4 | 4 | 0.5 | 1 | 1 | 4 | 4 | 2 | 8 | 0.06 |
| 223 | 4 | 8 | 8 | 4 | 4 | 0.5 | 0.5 | 0.5 | 4 | 4 | 2 | 8 | 0.06 |
| 224 | 4 | 4 | 4 | 4 | 1 | 1 | 0.5 | 0.5 | 4 | 4 | 2 | 16 | 0.06 |
| 225 | 4 | 4 | 4 | 4 | 4 | 0.5 | 0.5 | 0.25 | 2 | 2 | 2 | 16 | 2 |
| 226 | 4 | 4 | 2 | 4 | 4 | 0.5 | 0.25 | 0.5 | 4 | 4 | 1 | 16 | 0.06 |
| 227 | 2 | 2 | 4 | 4 | 4 | 0.25 | 0.25 | 0.25 | 2 | 2 | 1 | 8 | 2 |

TABLE 6-21

MIC against *Streptococcus dysgalactiae*

| # | A | B | C | D | E | F | G | H | I | J | K | L | M |
|---|---|---|---|---|---|---|---|---|---|---|---|---|---|
| 208 | 4 | 0.5 | 0.5 | 1 | >16 | 16 | 1 | 2 | 2 | 1 | 2 | 8 | 4 |
| 209 | 8 | 0.5 | 1 | 2 | >16 | >16 | 2 | 8 | 8 | 4 | 16 | >16 | 16 |
| 210 | 8 | 0.5 | 1 | 2 | >16 | >16 | 2 | 8 | 8 | 4 | 16 | >16 | >16 |
| 211 | 8 | ≤0.12 | 1 | 2 | >16 | >16 | 2 | 8 | 8 | 4 | 16 | >16 | >16 |
| 212 | 8 | 0.5 | 2 | 1 | >16 | >16 | 1 | 8 | 8 | 4 | 16 | >16 | >16 |
| 213 | 8 | 0.25 | 0.5 | 2 | >16 | >16 | 2 | 8 | 8 | 4 | 16 | >16 | 16 |
| 214 | 8 | 1 | 1 | 1 | >16 | 16 | 2 | 8 | 8 | 4 | 16 | >16 | 16 |
| 215 | 8 | 0.5 | 1 | 2 | >16 | 16 | 2 | 8 | 4 | 4 | 16 | >16 | 8 |
| 216 | 8 | 1 | 1 | 1 | >16 | 8 | 2 | 8 | 4 | 4 | 16 | >16 | 8 |
| 217 | 0.5 | 0.5 | 0.5 | 1 | >16 | >16 | 2 | 8 | 2 | 4 | 8 | >16 | 8 |

| # | N | O | P | Q | R | S | T | U | V | W | X | Y | Ery |
|---|---|---|---|---|---|---|---|---|---|---|---|---|-----|
| 208 | 4 | 4 | 2 | 4 | 4 | 0.5 | 0.5 | 0.5 | 4 | 2 | 4 | 4 | 0.06 |
| 209 | 8 | 8 | 16 | 4 | 8 | 1 | 1 | 1 | 8 | 8 | 8 | >16 | 0.06 |
| 210 | 16 | 8 | 16 | 4 | 8 | 1 | 1 | 1 | 8 | 8 | 8 | >16 | 0.12 |
| 211 | 16 | 8 | 8 | 4 | 8 | 1 | 1 | 1 | 8 | 8 | 8 | >16 | 0.06 |
| 212 | 16 | 8 | 16 | 8 | 4 | 1 | 1 | 2 | 8 | 8 | 8 | >16 | 0.12 |
| 213 | 8 | 8 | 8 | 4 | 8 | 0.5 | 1 | 1 | 8 | 8 | 8 | >16 | 0.12 |
| 214 | 8 | 8 | 8 | 4 | 4 | 1 | 1 | 2 | 8 | 8 | 8 | >16 | 0.06 |
| 215 | 8 | 8 | 8 | 4 | 8 | 0.5 | 0.5 | 1 | 8 | 4 | 4 | 16 | 0.12 |
| 216 | 8 | 8 | 8 | 4 | 8 | 1 | 1 | 1 | 8 | 8 | 8 | 16 | 0.06 |
| 217 | 8 | 8 | 4 | 4 | 8 | 1 | 0.5 | 1 | 8 | 4 | 4 | 16 | 0.12 |

Example 2. Minimum Inhibitory Concentration (MIC) in UHT Milk

The study was performed as described in Example 1, except UHT milk was used in place of broth. "MIC" is defined as the lowest antimicrobial concentration which did not allow a significant increase in bacterial concentration, as compared to the concentrations inoculated (less than 1 log of increase compared to inoculum). "MBC" is defined as the lowest concentration for which a decrease of at least 3 logs, compared to the concentration inoculated, was observed. Since the MIC in milk was expected to be ≥ the MIC in broth, concentrations between 0.12-32 µg/mL were tested. Isolates that were identified as typical were susceptibility-tested to three compounds (B, T, U). Overall, the compositions were active and stable in milk. In particular, two concentrations of the best-performing API (polymer B) retained their antimicrobial activity after having been filter-sterilized.

TABLE 7

Description of bacteria, media and incubation conditions for MIC tests

| | Susceptibility Testing Information | | | | |
|---|---|---|---|---|---|
| | | | Incubation | | |
| Organism | Repli-cates | Media | Temperature (° C.) | Atmo-sphere | Time (hr) |
| *Escherichia coli* (EC) | 3-5 | Milk | 36 ± 2 | Aerobic | 16-20 |
| *Mycoplasma bovis* (MB) | 3-5 | Milk | 36 ± 2 | Aerobic | 22-28 |
| *Staphylococcus aureus* (SA) | 3-5 | Milk | 36 ± 2 | Aerobic | 16-20 |
| *Staphylococcus aureus* (MRSA) | 3-5 | Milk | 36 ± 2 | Aerobic | 16-20 |
| *Streptococcus agalactiae* (SG) | 3-5 | Milk | 36 ± 2 | Aerobic | 20-24 |
| *Streptococcus dysgalactiae* (SY) | 3-5 | Milk | 36 ± 2 | Aerobic | 20-24 |
| *Streptococcus uberis* (SU) | 3-5 | Milk | 36 ± 2 | Aerobic | 20-24 |

Example 3. Evaluation of Ease of Administration and Retention of Various Formulations Three healthy, lactating adult Holstein cows, approximately 32 to 54 months of age, were studied to evaluate the acceptability and retention of various formulations of vehicles for intra-mammary infusion (versus saline). On Day 0, three mammary gland quarters from each of three lactating dairy cows were assigned to one of three treatments: Group 1 (LFQ)=8 mL saline; Group 2 (RFQ)=8 mL A0202-93A; Group 3 (LRQ)=8 mL A0202-93B. A0202-93A is a 2% w/w HPMC aqueous solution containing about 300 mg Polymer A per 8 mL; and A0202-93B is a 1.5% w/w HPMC solution containing about 300 mg Polymer B per 8 mL. Treatments were administered once intramammarily (IMM) for each quarter per animal for all treatment groups using disposable syringes. Daily health observations were conducted beginning on Day 0.

Ease of administration and infusion retention was determined at the time of treatment administration. Infusion retention and adverse reactions to treatment was determined at approximately 30 minutes post-treatment. Table 8 lists Animal Data, Treatment Ease of Administration and Infusion Retention scores. Table 9 lists Infusion Retention and Adverse Reactions, 30 Minutes Post-Treatment.

All treatment groups received Ease of Administration Scores of 1 (Acceptable; easy to administer) for all animals. Infusion retention scores for all treatment groups and all animals at the time of treatment administration and approximately 30 minutes post-treatment administration, was 1 (Retained). No adverse reactions due to treatment administration were observed at 30 minutes post-treatment.

TABLE 8

Animal Data, Treatment Ease of Administration and Infusion Retention

| ID | Mammary Gland Appearance | Quarter Infused (LF, RF, LR, RR)[1] | Group[2] | IMM Dose (mL) | Ease of Administration Score[3] | Infusion Retention Score[4] |
| --- | --- | --- | --- | --- | --- | --- |
| 2478 | Normal | LF | 1 | 8.0 | 1 | 1 |
|  |  | RF | 2 | 8.0 | 1 | 1 |
|  |  | LR | 3 | 8.0 | 1 | 1 |
| 1654 | Normal | LF | 1 | 8.0 | 1 | 1 |
|  |  | RF | 2 | 8.0 | 1 | 1 |
|  |  | LR | 3 | 8.0 | 1 | 1 |
| 2979 | Normal | LF | 1 | 8.0 | 1 | 1 |
|  |  | RF | 2 | 8.0 | 1 | 1 |
|  |  | LR | 3 | 8.0 | 1 | 1 |

[1] LF = Left front quarter (qtr), RF = Right front qtr, LR = Left rear qtr, RR = Right rear qtr
[2] Group 1 = 8 mL/qtr saline; Group 2 = 8 mL/qtr A0202-93A; Group 3 = 8 mL/qtr A0202-93B
[3] 1 = Acceptable (easy to administer); 2 = Unacceptable (Difficult to administer)
[4] 1 = Retained; 2 = Minimal drug loss; 3 = Moderate drug loss; 4 = Drug was not retained

TABLE 9

Infusion Retention and Adverse Reactions 30 Minutes Post-Treatment

| Animal ID | Mammary Gland Quarters Appearance (Normal/Abnormal) | Infusion Retention Score[1,2] | Adverse Reactions (clinical signs, etc.) |
| --- | --- | --- | --- |
| 2478 | All infused quarters normal | LF = 1 | No adverse reaction |
|  |  | RF = 1 | No adverse reaction |
|  |  | LR = 1 | No adverse reaction |
| 1654 | All infused quarters normal | LF = 1 | No adverse reaction |
|  |  | RF = 1 | No adverse reaction |
|  |  | LR = 1 | No adverse reaction |
| 2979 | All infused quarters normal | LF = 1 | No adverse reaction |
|  |  | RF = 1 | No adverse reaction |
|  |  | LR = 1 | No adverse reaction |

Example 4. Clinical Efficacy of the Antimicrobial Composition in Lactating Dairy Cattle Five lactating dairy cows, each having at least one quarter affected by acute mastitis, were sourced and enrolled into this study. On Days 0-2, the cows were administered 8 mL of the formulation (the "B" Polymer) in one mammary gland quarter. The formulation contained 3.75% w/v polymer B in a 1.75% HPMC aqueous solution. The formulation was evaluated for efficacy, safety, ease of administration and retention.

The intra-mammary infusions were administered after the PM milking and evaluated for ease of administration as well as retention immediately following administration. At 30 minutes post treatment (+15 minutes), retention and any adverse reactions to treatment were evaluated. A clinical evaluation of the animals was made once daily (at AM milking) during the study, including the evaluation of the mammary gland and milk (pre-milking). The four quarters of the cow's mammary gland were cultured (at AM milking) on Day 0 (pre-treatment) and on Days 3, 5, and 7. The cows were thus milked twice daily during the study.

Prior to treatment administration, the mammary gland quarters for each animal were individually evaluated. Only mammary gland quarters determined to have acute mastitis were used for administration (one quarter per cow). Eight mL of the formulation (containing 300 mg of API) were administered via IMM. A swab from each quarter was cultured on Day 0 (pre-infusion) and Days 3, 5, and 7. Similarly, a sample of the milk was cultured on both blood agar (5% sheep blood) supplemented with esculin, and *mycoplasma* agar. The agar plates were incubated at approximately 37° C. ($CO_2$ was added for the *mycoplasma* cultures). The blood agar was examined at 24 and 48 hours, and the *mycoplasma* agar was examined on 4 and 10 days post inoculation. The animals were evaluated as outlined in Table 10.

TABLE 10

Scoring system for evaluation of the animals

| | |
| --- | --- |
| Ease of Administration | 1 = Acceptable (easy) |
|  | 2 = Unacceptable (difficult) |
| Infusion Retention | 1 = Retained |
|  | 2 = Minimal loss |
|  | 3 = Moderate loss |
|  | 4 = Not retained |
| Swelling | 0 = Normal/Healthy |
|  | 1 = Slight Swelling |
|  | 2 = Moderate Swelling |
|  | 3 = Extremely Swollen |
| Pain (of the four quarters) | 0 = No |
|  | 1 = Yes |
| Milk Score (from four quarters) | 0 = Normal |
|  | 1 = Watery |
|  | 2 = Thick |
|  | 3 = Agalactic |

Partial milk scoring results were provided (swelling, pain and milk). One cow improved from (swelling 3; pain 1; milk 1) to all at "0" at day 7. About half of the treated cows demonstrated improvement, thus, higher levels of API and/or additional treatment days may be useful in completely eliminating the mastitis-causing infections. The well-tolerated, highly soluble antimicrobial polyamides are well-suited to such higher API level and longer term treatment regimens.

Example 5. Synthesis of Amine Functional Polyamides

Example 5-1: Synthesis of 4,4'-trimethylene dipiperidine bispropanoic acetate To 5.0 g of 4,4'-trimethylene dipiperidine in 20 mL of methanol solution (20 mL), 4.6 g of methyl acrylate was added drop-wise. The resulting reaction mixture was stirred at room temperature for 16 hours. The solvent was removed under reduced pressure and the residue was purified by column chromatography using a gradient solvent system comprising of from 100% hexane to 100% ethyl acetate. Removal of the solvent under reduced pressure yielded 7 g of the desired product as a white solid.

Example 5-2: Synthesis of 4,4'-dipiperidine bispropanoic acetate

To 10.0 g of 4,4'-dipiperidine HCl dissolved in 80 mL of methanol was added 12.6 g of potassium carbonate. The reaction mixture was stirred at room temperature for 3 hours, at which time 8.03 g of methyl acrylate was added slowly. The resulting reaction solution was then stirred at room temperature for 18 hours. The reaction mixture was filtered and the filtrate was evaporated to dryness under reduced pressure. The residue was treated with 300 mL of ethyl acetate. The resulting suspension was stirred at room temperature for 2 hours followed by filtration. The filtrate was evaporated to dryness under reduced pressure. The resulting mass was dried at room temperature under the vacuum to give 11.34 g of the desired product as an off white solid.

Example 5-3: Synthesis of Piperazine Bispropanoic Acetate

To 10 g of piperazine hexahydrate dissolved in 40 mL of methanol was added 9.97 g of methyl acrylate in a drop-wise manner. The reaction mixture was stirred at room temperature for 18 hours. At the end of this time, the reaction mixture was evaporated to dryness under reduced pressure. The residue was recrystallized from hexane/methylene chloride (1:1 v/v). After filtration and drying at room temperature under reduced pressure, 12.2 g of the desired product was obtained as a white solid.

Example 5-4: Synthesis of 1,1'-diacryl-4,4'-trimethylene dipiperidine

To 3.8 g of acryloyl chloride dissolved in 50 mL of dichloromethane was added a solution of 4.0 g of 4,4-trimethylene dipiperidine dissolved in 20 mL dichloromethane in a drop-wise manner at 0° C. To this solution was added 4.23 g of triethyl amine slowly with a syringe. The resulting reaction mixture was stirred for 18 hours and was allowed to warm to room temperature. The reaction mixture was filtered and the filtrate was collected. After removing the solvent under reduced pressure, the residue was treated with 100 mL of ethyl acetate. The solution was extracted with 1M HCl (1×100 mL), saturated NaHCO$_3$ (2×100 mL), and finally with brine (2×100 mL). The organic layer was collected and dried over Na$_2$SO$_4$. After filtration, the filtrate was evaporated to dryness under reduced pressure. The residue was purified by column chromatography using a gradient solvent system from 100% hexane to 100% ethyl acetate. Upon removal of the solvent, 3 g of the desired product was obtained as viscous oil.

Example 5-5: Synthesis of 2,2'-bipyrrolidine bispropanoic acetate

To a solution of 5 g of 2,2'-bipyrrolidine in 20 mL of methanol was added 6.9 g of methyl acrylate (6.9 g, 80 mmol) in a drop-wise manner. The resulting reaction mixture was stirred at room temperature for 16 hours. The reaction mixture was evaporated to dryness yielding 10 g of the desired product as viscous oil.

Example 5-6: Synthesis of poly (4,4'-trimethylene dipiperidine bispropanoic acid-co-1,3-diamino propane)

The reaction mixture consisting of 1 g of 4,4'-trimethylene dipiperidine bispropanoic acetate (Example 5-1) and 0.387 g of 1,3-diamino propane was heated at 100° C. under nitrogen atmosphere for 18 hours. The resulting product was dissolved in 5 mL of dichloromethane and was poured into 50 mL of ethyl acetate. After filtering off the solvent, the residue was dissolved in 20 ml, of deionized (DI) water. The pH of the solution was brought to 2 by addition of HCl. The resulting solution was dialyzed against DI water for 24 hours using a dialysis membrane of molecular weight cut off of 1000 Da. The solution remaining in the dialysis bag was dried by lyophilization yielding 90 mg of the desired product as a light yellow solid.

Example 5-7: Synthesis of poly (4,4'-trimethylene dipiperidine bispropanoic acid-co-diamino ethane)

The reaction mixture containing 0.5 g of 4,4'-trimethylene dipiperidine bispropanoic acetate (Example 5-1) and 0.157 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 50 mg of the desired product as a light yellow solid.

Example 5-8: Synthesis of poly (4,4'-trimethylene dipiperidine bispropanoic acid-co-1,4-diamino butane)

The reaction mixture containing 0.5 g of 4,4'-trimethylene dipiperidine bispropanoic acetate and 0.23 g of 1,4-diamino butane was stirred at 100° C. under nitrogen atmosphere for 18 hours. The resulting product was dissolved in 5 mL of CH$_2$Cl$_2$ and then precipitated in 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-9: Synthesis of poly (4,4'-trimethylene dipiperidine bispropanoic acid-co-1,2-bis (2-aminoethoxy) ethane The reaction mixture containing 0.5 g of 4,4'-trimethylene dipiperidine bispropanoic acetate and 0.26 g of 1,2-bis(2-aminoethoxy) ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-10: Synthesis of poly (4,4'-trimethylene dipiperidine bispropanoic acid-co-1,4-bis(aminomethyl) benzene The reaction mixture containing 0.5 g of 4,4'-trimethylene dipiperidine bispropanoic acetate and 0.7 g of 1,4-bis(aminomethyl) benzene (0.7 g, 5.1 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 40 mg of the desired product as a light yellow solid.

Example 5-11: Synthesis of poly (4,4'-trimethylene dipiperidine bispropanoic acid-co-2,2'diamino diethylamine The reaction mixture containing 0.5 g of 4,4'-trimethylene dipiperidine bispropanoic acetate and 0.35 g of 2,2'diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 63 mg of the desired product as a light yellow solid.

Example 5-12: Synthesis of poly (4,4'-trimethylene dipiperidine bispropanoic acid-co-N-methyl-2,2'diamino diethylamine The reaction mixture containing 1 g of 4,4'-trimethylene dipiperidine bispropanoic acetate and 0.61 g of N-methyl-2,2'diamino diethylamine (0.61 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 130 mg of the desired product as a light yellow solid.

Example 5-13: Synthesis of poly (4,4'-trimethylene dipiperidine bispropanoic acid-co-N-(3-aminopropyl)-1,3-propane diamine The reaction mixture containing 1 g of 4,4'-trimethylene dipiperidine bispropanoic acetate and 0.68 g of N-(3-aminopropyl)-1,3-propane diamine (0.68 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 180 mg of the desired product as a light yellow solid.

Example 5-14: Synthesis of poly (4,4'-trimethylene dipiperidine bispropanoic acid-co-3,3'-diamino-N-methyl dipropylamine The reaction mixture containing 1 g of 4,4'-trimethylene dipiperidine bispropanoic acetate and 0.76 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 110 mg of the desired product as a light yellow solid.

Example 5-15: Synthesis of poly (4,4'-trimethylene dipiperidine bispropanoic acid-co-1,3-diamino-2-propanol The reaction mixture containing 1 g of 4,4'-trimethylene dipiperidine bispropanoic acetate and 0.47 g of 1,3-diamino-2-propanol (0.47 g, 5.2 mmol) was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-16: Synthesis of poly (4,4'-trimethylene dipiperidine bispropanoic acid-co-4-(4-amino-butoxyl)-butyl amine 4-(4-amino-butoxyl)-butyl amine HCl salt (1 g) was dissolved in 20 mL of methanol. To this solution 0.72 g of aqueous sodium hydroxide solution (50% w/w)) was added. The reaction mixture was stirred at room temperature for 1 hour. After filtering off the solids, the filtrate was evaporated to dryness. The residue was treated with 20 mL of ethanol.

The reaction mixture was filtered and the filtrate was evaporated to dryness yielding 0.55 g of an off white solid. This solid was combined with 0.75 g of 4,4'-trimethylene dipiperidine bispropanoic acetate and the resulting reaction mixture was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 90 mg of the desired product as a light yellow solid.

Example 5-17: Synthesis of poly (4,4'-trimethylene dipiperidine bispropanoic acid-co-3,5-diamino-1,2,4-triazol The reaction mixture containing 1 g of 4,4'-trimethylene dipiperidine bispropanoic acetate and 0.31 g of 3,5-diamino-1,2,4-triazole was treated with 1 mL of DMSO. The resulting reaction mixture was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 10 mg of the desired product as a light yellow solid.

Example 5-18: Synthesis of poly (piperazine bispropanoic acid-co-diamino ethane)

The reaction mixture containing 1 g of piperazine bispropanoic acetate (Example 5-3) and 0.47 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 10 mg of the desired product as a light yellow solid.

Example 5-19: Synthesis of poly(piperazine bispropanoic acid-co-1,3-diamino propane)

The reaction mixture containing 1 g of piperazine bispropanoic acetate (Example 5-3) and 0.5 g of 1,3-diamino propane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 30 mg of the desired product as a light yellow solid.

Example 5-20: Synthesis of poly (piperazine bispropanoic acid-co-1,4-diamino butane)

The reaction mixture containing 1 g of piperazine bispropanoic acetate (Example 5-3) and 0.6 g of 1,4-diamino butane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-21: Synthesis of poly (piperazine bispropanoic acid-co-1,2-bis(2-aminoethoxy) ethane The reaction mixture containing 1 g of piperazine bispropanoic acetate (Example 5-3) and 1.15 g of 1,2-bis(2-aminoethoxy) ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 30 mg of the desired product as a light yellow solid.

Example 5-22: Synthesis of poly (piperazine bispropanoic acid-co-2,2'diamino diethylamine The reaction mixture containing 1 g of piperazine bispropanoic acetate (Example 5-3) and 0.8 g of 2,2'-diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-23: Synthesis of poly (piperazine bispropanoic acid-co-N-methyl-2,2'diamino diethylamine The reaction mixture containing 1 g of piperazine bispropanoic acetate (Example 5-3) and 0.9 g of N-methyl-2,2'-diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 50 mg of the desired product as a light yellow solid.

Example 5-24: Synthesis of poly (piperazine bispropanoic acid-co-N-(3-aminopropyl)-1,3-propane diamine The reaction mixture containing 1 g of piperazine bispropanoic acetate (Example 5-3) and 1.02 g of N-(3-aminopropyl)-1,3-propane diamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 90 mg of the desired product as a light yellow solid.

Example 5-25: Synthesis of poly (piperazine bispropanoic acid-co-3,3'-diamino-N-methyl dipropylamine The reaction mixture containing 1 g of piperazine bispropanoic acetate (Example 5-3) and 1.12 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 120 mg of the desired product as a light yellow solid.

Example 5-26: Synthesis of poly (4,4'-dipiperidine bispropanoic acid-co-diamino ethane The reaction mixture containing 1 g of 4,4'-dipiperidine bispropanoic acetate (Example 5-2) and 0.31 g of diamino ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 90 mg of the desired product as a light yellow solid.

Example 5-27: Synthesis of poly (4,4'-dipiperidine bispropanoic acid-co-1,3-diamino propane The reaction mixture containing 1 g of 4,4'-dipiperidine bispropanoic acetate (Example 5-2) and 0.38 g of 1,3-diamino propane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 60 mg of the desired product as a light yellow solid.

Example 5-28: Synthesis of poly (4,4'-dipiperidine bispropanoic acid-co-1,4-diamino butane The reaction mixture containing 1 g of 4,4'-dipiperidine bispropanoic acetate (Example 5-2) and 0.45 g of 1,4-diamino butane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 90 mg of the desired product as a light yellow solid.

Example 5-29: Synthesis of poly (4,4'-dipiperidine bispropanoic acid-co-1,2-bis (2-aminoethoxy) ethane The reaction mixture containing 1 g of 4,4'-dipiperidine bispropanoic acetate (Example 5-2) and 0.76 g of 1,2-bis (2-aminoethoxy) ethane was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 100 mg of the desired product as a light yellow solid.

Example 5-30: Synthesis of poly (4,4'-dipiperidine bispropanoic acid-co-2,2'diamino diethylamine The reaction mixture containing 1 g of 4,4'-dipiperidine bispropanoic acetate and 0.45 g of 2,2'diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 310 mg of the desired product as a light yellow solid.

Example 5-31: Synthesis of poly (4,4'-dipiperidine bispropanoic acid-co-N-methyl-2,2'diamino diethylamine The reaction mixture containing 1 g of 4,4'-dipiperidine bispropanoic acetate and 0.52 g of N-methyl-2,2'diamino diethylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 480 mg of the desired product as a light yellow solid.

Example 5-32: Synthesis of poly (4,4'-dipiperidine bispropanoic acid-co-N-(3-aminopropyl)-1,3-propane diamine The reaction mixture containing 1 g of 4,4'-dipiperidine bispropanoic acetate and 0.58 g of N-(3-aminopropyl)-1,3-propane diamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 540 mg of the desired product as a light yellow solid.

Example 5-33: Synthesis of poly (4,4'-dipiperidine bispropanoic acid-co-3,3'-diamino-N-methyl dipropylamine The reaction mixture containing 1 g of 4,4'-dipiperidine bispropanoic acetate and 0.64 g of 3,3'-diamino-N-methyl dipropylamine was stirred at 100° C. under nitrogen atmosphere for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 420 mg of the desired product as a light yellow solid.

Example 5-34: Synthesis of Poly (1,1'-diacryl-4,4'-trimethylene dipiperidine-co-1,3-diaminopropane The reaction mixture containing 1 g of 1,1'-diacryl-4,4'-trimethylene dipiperidine, 0.35 g 1,3-diamino propane and 1 mL of methanol was stirred at room temperature for 18 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 640 mg of the desired product as a light yellow solid.

Example 5-35: Synthesis of poly (1,1'-diacryl-4,4'-trimethylene dipiperidine-co-N,N'-dimethyl-1,3-propanediamine The reaction mixture containing 1 g of 1,1'-diacryl-4,4'-trimethylene dipiperidine, 0.36 g of N,N'-dimethyl-1,3-propanediamine and 1 mL of methanol was stirred at 60° C. for 24 hours. The solvent was removed under reduced pressure and the residue was dissolved in 20 mL of DI water. The pH of the solution was adjusted to 2 by adding HCl. The polymer solution dialyzed against DI water using a dialysis membrane of molecular weight cut off of 1000 Da. The solution remaining in the dialysis membrane was lyophilized to dryness yielding 180 mg of the desired product as a light yellow solid.

Example 5-36: Synthesis of poly (1,1'-diacryl-4,4'-trimethylene dipiperidine-co-4,4'-trimethylene dipiperidine The reaction mixture containing 1 g of 1,1'-diacryl-4,4'-trimethylene dipiperidine, 0.99 g of 4,4'-trimethylene dipiperidine, 1 mL of methanol was stirred at 60° C. for 12 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 220 mg of the desired product as a light yellow solid.

Example 5-37: Synthesis of poly (1,1'-diacryl-4,4'-trimethylene dipiperidine-co-piperazine The reaction mixture containing 1 g of 1,1'-diacryl-4,4'-trimethylene dipiperidine, 0.91 g of piperazine hexahydrate and 1 mL of methanol was stirred at 60° C. for 12 hours. The resulting product was dissolved in 5 mL of dichloromethane and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 80 mg of the desired product as a light yellow solid.

Example 5-38: Synthesis of poly (1,1'-diacryl-4,4'-trimethylene dipiperidine-co-4,4'-bipiperidine A solution containing 1.14 g of 4,4'-dipiperidine HCl and 5 mL of methanol was treated with 1.14 g of potassium carbonate. The reaction mixture was stirred at room temperature for 2 hours. The reaction mixture was filtered and the filtrate was combined with 1 g of 1,1'-diacryl-4,4'-trimethylene dipiperidine dissolved in 3 mL of methanol. The resulting reaction mixture was stirred at 60° C. for 15 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 140 mg of the desired product as a light yellow solid.

Example 5-39: Synthesis of poly (1,1'diacryl-4,4'-trimethylene dipiperidine-co-histamine)

The reaction mixture containing 1 g of 1,1'-diacryl-4,4'-trimethylene dipiperidine, 0.5 g of histamine and 1 mL of methanol was stirred at 60° C. for 18 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 120 mg of the desired product as a light yellow solid.

Example 5-40: Synthesis of poly (1,1'diacryl-4,4'-trimethylene dipiperidine-co-3-(dimethylamino)-1-propylamine)

The reaction mixture containing 1 g of 1,1'-diacryl-4,4'-trimethylene dipiperidine, 0.53 g of 3-(dimethylamino)-1-propylamine and 1 mL of methanol was stirred at 50° C. for 10 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 1 g of the desired product as a light yellow solid.

Example 5-41: Synthesis of poly (1,1'diacryl-4,4'-trimethylene dipiperidine-co-propyl amine The reaction mixture containing 0.64 g of 1,1'-diacryl-4,4'-trimethylene dipiperidine, 0.35 g of propyl amine, and 1 mL methanol was stirred at 60° C. for 20 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 740 mg of the desired product as a light yellow solid.

Example 5-42: Synthesis of poly (1,1'diacryl 4,4'-trimethylene dipiperidine-co-1-aminobutyl-3-carbamoyl pyridinium The reaction mixture containing 0.5 g of 1,1'-diacryl-4,4'-trimethylene dipiperidine, 0.35 g of 1-aminobutyl-3-carbamoyl pyridinium, and 3 mL of methanol was stirred at 50° C. for 20 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 20 mg of the desired product as a light yellow solid.

Example 5-43: Synthesis of poly (1,1'diacryl-4,4'-trimethylene dipiperidine-co-1-aminobutyl-3-carbamoyl pyridinium)-co-4,4'-trimethylene dipiperidine bispropanoic acid-2-dydroxy-1,3-diamino propane)

The reaction mixture containing 1.0 g of 1,1'-diacryl-4,4'-trimethylene dipiperidine, 0.36 g of 1-aminobutyl-3-carbamoyl pyridinium, 0.27 g of mono N-boc-1,3-diaminopropane, and 3 mL of methanol stirred at 50° C. for 20 hours. The reaction mixture was poured into 50 mL of ethyl acetate. The precipitate was isolated by filtration. The residue was washed with ethyl acetate (3×50 mL) and dried under reduced pressure.

Above product was dissolved in 5 mL of methanol and mixed with 0.5 g of 4,4'-trimethylene dipiperidine bispropanoic acid and 0.25 mL of concentrated HCl. The resulting reaction mixture was stirred at 50° C. for 6 hours. The resulting product was poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 210 mg of the desired product as a light yellow solid.

Example 5-44: Synthesis of poly (2,2'-bipyrrolidine bispropanoic acid-co-diamino ethane)

The reaction mixture containing 1.0 g of 2,2'-bipyrrolidine bispropanoic acetate and 0.38 g diamino ethane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 10 mg of the desired product as a light yellow solid.

Example 5-45: Synthesis of poly (2,2'-bipyrrolidine bispropanoic acid-co-1,3-diamino propane)

The reaction mixture containing 1.0 g of 2,2'-bipyrrolidine bispropanoic acetate and 0.47 g of 1,3-diamino propane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 540 mg of the desired product as a light yellow solid.

Example 5-46: Synthesis of poly (2,2'-bipyrrolidine bispropanoic acid-co-1,3-diamino butane)

The reaction mixture containing 1.0 g of 2,2'-bipyrrolidine bispropanoic acetate and 0.56 g of 1,4-diamino butane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 380 mg of the desired product as a light yellow solid.

Example 5-47: Synthesis of poly (2,2'-bipyrrolidine bispropanoic acid-co-1,5-diamino pentane)

The reaction mixture containing 1.0 g of 2,2'-bipyrrolidine bispropanoic acetate and 0.65 g of 1,5-diamino pentane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 10 mg of the desired product as a light yellow solid.

Example 5-48: Synthesis of poly (2,2'-bipyrrolidine bispropanoic acid-co-1,6-diamino hexane)

The reaction mixture containing 1.0 g of 2,2'-bipyrrolidine bispropanoic acetate and 0.74 g of 1,6-diamino hexane was stirred at 100° C. under nitrogen atmosphere for 20 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 10 mg of the desired product as a light yellow solid.

Example 5-49: Synthesis of poly (4,4-Trimethylene dipiperidine bispropanoic acid-co-4-(1,2-diol)-1,4,7-triazaheptane)

Example 5-49(a)

Synthesis of 4-(1,2-diol)-1,4,7-triazaheptane

In 5 mL of ethanol 1 g of 1,7-bis-Boc-1,4,7-triazaheptane and 0.3 g of glycidol were added and the reaction mixture was refluxed for 15 hours. The resulting product was purified by column chromatography using gradient solvent system in the range of 100% hexane to 100% yielding 0.4 g of 1,7-bis-boc-4-(1,2-diol)-1,4,7-triazaheptane. To 0.4 g of 1,7-bis-boc-4-(1,2-diol)-1,4,7-triazaheptane dissolved in 2 mL of methanol was added 0.3 mL of concentrated HCl. The reaction mixture was stirred at 50° C. for 24 hours. After removing the solvent under reduced pressure, the residue was dissolved in 10 mL of methanol:water (1:1 v/v). To this solution was added 5.0 g of Amberlyst OH 26 resin. After stirring at room temperature for 3 hours, the resin was filtered off. The solvent was evaporated under reduced pressure. The resulting oil was lyophilized to dry to give 0.15 g of the desired product as a viscous liquid.

Example 5-49(b)

Synthesis of poly(4,4-Trimethylene dipiperidine bispropanoic acid-co-4-(1,2-diol)-1,4,7-triazaheptane)

The reaction mixture containing 0.288 g of 4,4'-trimethylene dipiperidine bispropanoic acetate and 0.15 g of 4-(1,2-diol)-1,4,7-triazaheptane (Example 5-49(a)) stirred at 100° C. for 18 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 160 mg of the desired product as a light yellow solid.

Example 5-50: Synthesis of poly (4,4-trimethylene dipiperidine bispropanoic acid-co-4-(1,2-diol)-1,4,7-triazaheptane-co-1,3-diamino propane)

The reaction mixture containing 0.25 g of 4,4'-trimethylene dipiperidine bispropanoic acetate, 0.09 g of 4-(1,2-diol)-1,4,7-triazaheptane (Example 5-49(a)) and 0.05 g of 1,3-diamino propane stirred at 100° C. for 18 hours. The resulting product was dissolved in 3 mL of methanol and poured into 50 mL of ethyl acetate. The precipitate was isolated by filtration and was dissolved in 20 mL of DI water. After adjusting the pH of the solution to 2, it was dialyzed against DI water using a dialysis membrane of molecular weight cut off of 1000 Da. The solution remaining in the dialysis membrane was lyophilized to dryness yielding 150 mg of the desired product as a light yellow solid.

Example 5-51: Synthesis of poly (4,4-Trimethylene dipiperidine bispropanoic acid-co-5-(1,2-diol)-1,5,9-triazanonane)

Example 5-51(a)

Synthesis of 5-(1,2-diol)-1,5,9-triazanonane

The reaction mixture containing 1.5 g of 1,9-Bis-BOC-1,5,9-triazanonane, 0.34 g of glycidol, and 10 mL of ethanol was refluxed for 15 hours. After removal of the solvent, the residue was purified by column chromatography using a gradient solvent system ranging from 100% hexane to 100% ethyl acetate) yielding 0.7 g of 1,9-bis-boc-5-(1,2-diol)-1,5,9-triazanonane. To 0.7 g of 1,9-bis-boc-5-(1,2-diol)-1,5,9-triazanonane dissolved in 2 mL of methanol was added 0.25 mL of concentrated HCl and the reaction mixture stirred at 50° C. for 24 hours. After removal of the solvent under reduced pressure, the residue was dissolved in 10 mL of methanol/water (1:1) mixture and 5 g of Amberlyst OH 26 resin was added it. After stirring at room temperature for 3 hours, the resin was filtered off. The solvent was removed under reduced pressure and the residue was lyophilized to dryness yielding 0.28 g of the desired product as light yellow oil.

Example 5-51(b)

Synthesis of poly(4,4-Trimethylene dipiperidine bispropanoic acid-co-5-(1,2-diol)-1,5,9-triazanonane)

The reaction mixture containing 0.23 g of 4,4'-trimethylene dipiperidine bispropanoic acetate and 0.15 g of 5-(1,2-diol)-1,5,9-triazanonane was stirred at 100° C. for 18 hours. The resulting reaction mixture was dissolved in 5 mL of methanol and poured into 50 mL of ethyl acetate. After filtering off the solvent, the residue was dissolved in 20 mL of DI water. The pH of the solution was adjusted to 2 by adding dilute HCl and the solution subjected to centrifugation using with Microsep membrane filter with a molecular weight cut off of 1000 Da. The fraction with molecular weight higher than 1000 Da was collected and lyophilized to dryness yielding 100 mg of the desired product as a light yellow solid.

Example 5-52: Synthesis of poly (4,4-trimethylene dipiperidine bispropanoic acid-co-5-(1,2-diol)-1,5,9-triazanonane-co-1,3-diamino propane)

The reaction mixture containing 0.125 g 4,4'-trimethylene dipiperidine bispropanoic acetate (Example 5-1), 0.05 g of 5-(1,2-diol)-1,5,9-triazanonane (Example 5-51(a)), and 0.3 g of 1,3-diamino propane was stirred at 100° C. for 18 hours. The resulting reaction mixture was dissolved in 5 mL of methanol poured into 50 mL of ethyl acetate. After filtering off the solvent, the residue was dissolved in 20 mL of DI water. The pH of the solution was adjusted to 2 by adding dilute HCl and the solution subjected to centrifugation using with Microsep membrane filter with a molecular weight cut off of 1000 Da. The fraction with molecular weight higher than 1000 Da was collected and lyophilized to dryness yielding 90 mg of the desired product as a light yellow solid.

Example 5-53: Synthesis of glycidol modified poly (4,4'-trimethylene dipiperidine bispropanoic acid-co-1,3-diamino propane)

To 0.26 g poly (4,4'-trimethylene dipropanoic acid-co-1,3-diamino propane) (Example 5-6) dissolved in 2 mL of ethanol was added 16.5 mg of glycidol. The reaction mixture at 140° C. for 30 minutes using a microwave reactor. The resulting reaction mixture was poured into 50 mL of ethyl acetate. After filtration, the residue was washed with ethyl acetate (3×50 mL). Subsequently, it was dissolved in 10 mL of DI water and was subjected to centrifugation using with Microsep membrane filter with a molecular weight cut off of 1000 Da. The fraction with molecular weight higher than 1000 Da was collected and lyophilized to dryness yielding 126 mg of the desired product as a light yellow solid.

Example 5-54: Synthesis of Guanidine terminated poly (4,4'-trimethylene dipiperidine bispropanoic acid-co-1,3-diamino propane)

To 0.3 g of poly (4,4'-trimethylene dipiperidine bispropanoic acid-co-1,3-diamino propane) (Example 5-6) dissolved in 2 mL of methanol was added 0.1 g of 1H-pyrazole-1-carboxamidine and 0.11 g of N,N'-diisopropylethylamine. The reaction mixture was stirred at 60° C. for 8 hours. The resulting reaction mixture was poured into 50 mL of ethyl acetate. After filtration, the residue was washed with ethyl acetate (3×50 mL). The resulting solid was dissolved in 2 mL of DI water and was passed through a PD-10 Sephadex column. The desired fractions were collected, lyophilized to dryness yielding 0.19 g of the polymer as a light yellow solid.

Example 5-55: Synthesis of Polyethylene glycol (PEG-4) terminated poly (4,4'-trimethylene dipiperidine bispropanoic acid-co-1,3-diamino propane)

To 0.128 g of poly (4,4'-trimethylene dipiperidine bispropanoic acid-co-1,3-diamino propane) (Example 5-6) dissolved in 5 mL of methanol was added 0.2 mL of triethyl amine followed by 0.075 g of m-dPEG4-NHS ester. The reaction solution was stirred at room temperature for 22 hours. The resulting reaction mixture was poured into 50 mL of ethyl acetate. After filtration, the residue was washed with ethyl acetate (5×50 mL). The residue was subsequently dissolved in 2 mL of DI water and the pH of the resulting solution was adjusted to 2 using dilute HCl was subjected to centrifugation using a Microsep membrane filter with a molecular weight cut off of 1000 Da. The fraction with molecular weight higher than 1000 Da was collected and lyophilized to dryness yielding 50 mg of the desired product as a light yellow solid.

Example 5-56: Synthesis of Polyethylene glycol (PEG-12) terminated poly (4,4'-trimethylene dipiperidine bispropanoic acid-co-1,3-diamino propane)

To 0.1 g of poly (4,4'-trimethylene dipiperidine bispropanoic acid-co-1,3-diamino propane) (Example 5-6) dissolved 5 mL of methanol was added 0.2 mL of triethyl amine followed by 0.12 g of m-dPEG12-NHS ester. The reaction solution was stirred at room temperature for 22 hours. The resulting reaction mixture was poured into 50 mL of ethyl acetate. After filtration, the residue was washed with ethyl acetate (5×50 mL). The residue was subsequently dissolved in 2 mL of DI water and the pH of the resulting solution was adjusted to 2 using dilute HCl. was subjected to centrifugation using with Microsep membrane filter with a molecular weight cut off of 1000 Da. The fraction with molecular weight higher than 1000 Da was collected and lyophilized to dryness yielding 60 mg of the desired product as a light yellow solid.

Example 5-57: Synthesis of monodispersed polymer (heptamer) of poly(4,4'-trimethylene dipiperidine bispropanoic acid-co-1,3-diamino propane)

Example 5-57(a)

Synthesis of 4,4'-trimethylene dipiperidine bispropanoic acid-1,3-diamino propane trimer The reaction mixture containing 3 g of 4,4'-trimethylene dipiperidine bispropanoic acetate (Example 5-2) and 4.1 g of mono N-boc-1,3-diamino propane was stirred at 100° C. for 18 hours. The resulting reaction mixture was purified by column chromatography using an amine modified silica column and the gradient solvent system ranging from 100% hexane to ethyl acetate/hexane (50/50)). The appropriate fraction was collected and removal of the solvent under reduced pressure produced 2.6 g of 4,4'-trimethylene dipiperidine bispropanoic acid-bis-BOC-1,3-diamino propane.

To 0.55 g of 4,4'-trimethylene dipiperidine bispropanoic acid-bis-boc-1,3-diamino propane dissolved in 5 mL of methanol was added 0.5 mL of concentrated HCl and the reaction mixture was stirred at 50° C. for 10 hours. After removal of the solvent under reduced pressure, the residue was dissolved in 10 mL of methanol/water (1:1) and was treated with 5 g of Amberlyst OH 26 resin. After stirring at room temperature for 3 hours, the resin was filtered off. The filtrate was evaporated dryness and the residue was lyophilized yielding 0.5 g of the product as a white solid.

Example 5-57(b)

Synthesis of 1-BOC-4,4'-trimethylene-1'-propanoic acid

To 2 g of 1-BOC-4,4'-trimethylene-1'propanoic methyl ester, 0.9 g of 50 wt % solution of aqueous sodium hydroxide was added and the reaction mixture was stirred at 60° C. for 15 hours. To this reaction mixture was added concentrated HCl until pH of the reaction reached 7.5. The reaction mixture was evaporated to dryness and residue was lyophilized to complete dryness. To this dry residue was added 10 mL of dichloromethane and the resulting mixture was stirred at room temperature for 30 minutes. After filtering off the insoluble particles, the filtrate was evaporated to dryness to give 0.7 g of a white solid product.

Example 5-57(c)

Synthesis of bis-boc-4,4'-trimethylene dipiperidine bispropanoic acid-1,3-diamino propane pentamer To 90 mg of 1-boc-4,4'-trimethylene-1'-propanoic acid (Example 5-57(b)) dissolved in 2 mL of dicloromethane/DMF (1:1 v/v) was added 38 mg of 1,1-carbonyl diimidazole. After stirring at room temperature for 1 hour, 0.05 g of 4,4'-trimethylene dipiperidine bispropanoic acid-1,3-diamino propane trimer (Example 5-57(a)) was added to reaction mixture. The resulting reaction mixture was stirred at room temperature for 20 hours. After removing the solvent under reduced pressure, the residue was purified by column chromatography using an amine modified silica column using a gradient solvent system ranging from 100% ethyl acetate to ethyl acetate/methanol (95/5)) yielding 80 mg of the product as a colorless oil. This oil was dissolved 2 mL of methanol followed by addition of 0.5 mL of concentrated HCl. The reaction mixture was stirred at 50° C. for 10 hours. The solvent was evaporated removed under reduced pressure and the residue was lyophilized to dry to yield 60 mg of the desired product as yellow viscous oil.

Example 5-57(d)

Synthesis of poly(4,4'-trimethylene dipiperidine bispropanoic acid-co-1,3-diamino propane) heptamer To 35 mg of 4,4'-trimethylene dipiperidine bispropanoic acid-1,3-diamino propane pentamer (Example 5-57(c)) dissolved in 1 mL of methanol was added 0.08 mL of triethyl amine and 24 mg of boc-(3-acrylamido) propyl amine. The reaction mixture was stirred at room temperature overnight. The reaction mixture was poured into 10 mL of ethyl acetate. The residue was isolated by filtration and was washed with ethyl acetate (3×10 mL). The residue was dried at room temperature under reduced pressure yielding 40 mg of a white solid. To this solid residue was added 2 mL of methanol and 0.5 mL of concentrated HCl. The resulting reaction mixture was added stirred at 50° C. for 10 hours. After removing the solvent under reduced pressure, residue was purified by preparative HPLC yielding 10 mg of the desired product as light yellow viscous oil.

Having thus described in detail preferred embodiments of the present invention, it is to be understood that the invention defined by the above examples is not to be limited to particular details set forth in the above description as many apparent variations thereof are possible without departing from the spirit or scope of the present invention.

What is claimed is:

1. A veterinary composition for treating infections in non-human animals, comprising a suitable veterinary carrier and at least one antimicrobial polyamide: and wherein the polyamide is present in a bactericidally effective amount, wherein the composition is effective in treating infections or disease states caused by at least one of the following pathogens selected from the group consisting of *Staphylococcus* spp., *Streptococcus* spp., *Mycoplasma bovis*, and *E. coli*, wherein the polyamide is selected from the group consisting of:

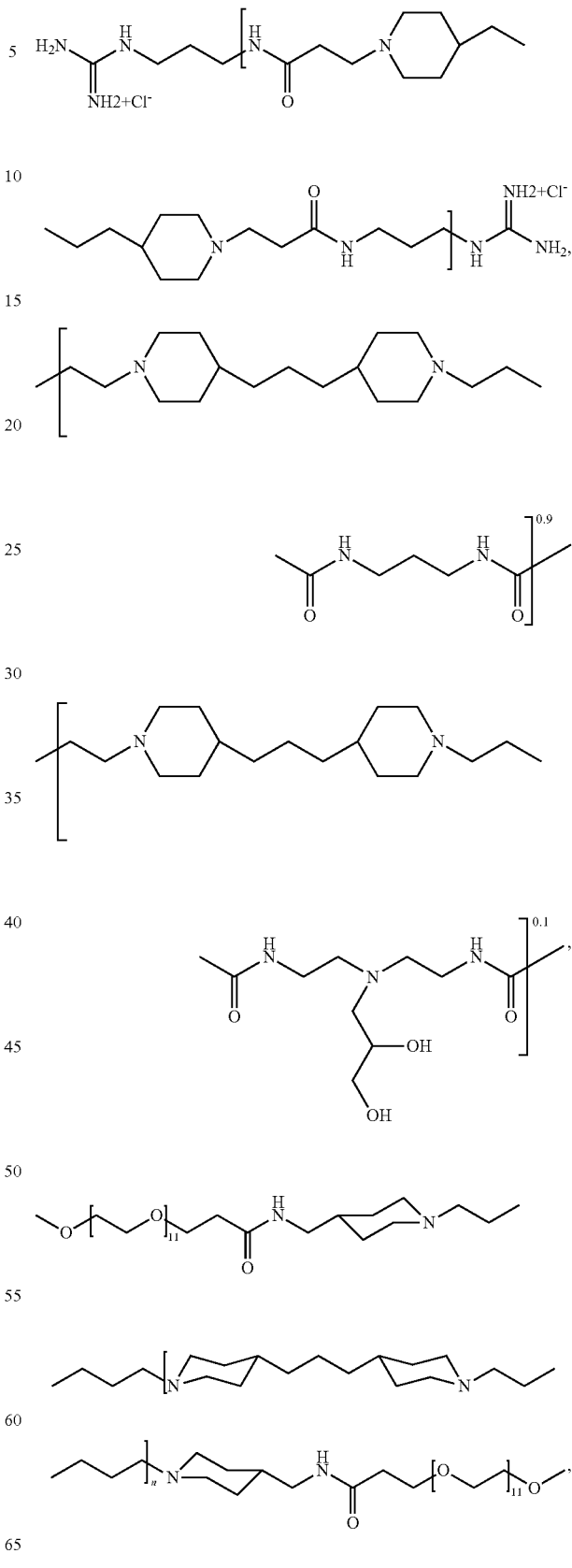

and combinations thereof.

2. The veterinary composition of claim 1, wherein the polyamide has the following structure:

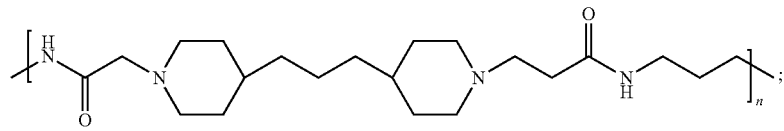

and wherein the weight average molecular weight (WAMW) is from about 1.0 kDa to about 15.0 kDa, as measured by size exclusion chromatography.

3. The veterinary composition of claim 2, wherein the polyamide has a WAMW from about 2.0 kDa to about 10 kDa.

4. The veterinary composition of claim 2, wherein the polyamide has a WAMW from about 2.5 kDa to about 7.76 kDa, or has a WAMW of about 7.76 kDa.

5. The veterinary composition of claim 1, wherein one dose of the composition, for the treatment of one udder quarter, contains from about 20 to about 3000 mg of the polyamide.

6. The veterinary composition of claim 5, wherein the dose contains from about too to about 2000 mg; from about 200 to about 1500 mg; from about 250 to about 1000 mg; from about 300 to about 500 mg; or about 300 mg of the polyamide.

7. The veterinary composition of claim 6, wherein the dose contains from about 300 to about 500 mg of the polyamide.

8. The veterinary composition of claim 1, wherein the veterinarily acceptable carrier comprises a thickener or rheology modifier (TRM).

9. The veterinary composition of claim 8, wherein the TRM is selected from the group consisting of any acceptable cellulose derivative, methyl cellulose (MC), ethylcellulose (EC), EC N50, hydroxymethyl cellulose (HMC), hydroxypropyl cellulose (HPC), hydroxypropyl methyl cellulose (HPMC), hydroxyethyl cellulose (HEC), polyethylene glycols (PEGs), poloxamers, block copolymers, cross-linked acrylic acid-based polymers, carbomers, CARBOPOL polymers, alkali-swellable emulsion (ASE) polymers, polysaccharides, modified polysaccharides, modified starches, partially or pre-gelatinized starch, aluminum stearate, 12-hydroxystearin, THIXCIN, beeswax, emulsifying waxes, hydrogenated peanut oil, castor oil, hydrogenated castor oil, hard/soft paraffin, metal salts of fatty acids, mucoadhesives, alkyl triammonium methosulfate, ceteraryl octanoate, polyvinyl alcohol, chitosan, chitosan derivatives, trimethylated chitosan, xanthum gum, guar gum, hyaluronic acid, thermogelling agents, shear-thinning agents, shear-gelling agents, polycarbophil, polyethylene oxide, silica, fumed silica, any fumed metal oxide, non-toxic heavy metal salts, hydrogenated oils, hydrogenated castor oil and combinations thereof.

10. The veterinary composition of claim 9, wherein the TRM is a cellulose derivative selected from the group consisting of methyl cellulose (MC), ethylcellulose (EC), EC N50, hydroxymethyl cellulose (HMC), hydroxypropyl cellulose (HPC), hydroxypropyl methyl cellulose (HPMC), hydroxyethyl cellulose (HEC), and combinations thereof.

11. The veterinary composition of claim 10, wherein the composition has a viscosity (measured at 20° C.) from about 200 cP to about 8,000 cP or from about 4,000 cP to about 6,000 cP; and wherein the viscosity is measured using a spindle viscometer.

12. The veterinary composition of claim 11, wherein the TRM is HPMC having a WAMW of about 86 kDa, a methoxyl content of about 28 to about 30% and a hydroxypropoxyl content of about 7 to about 12% of the HPMC; and wherein the HPMC has the CAS number 9004-65-3.

13. The veterinary composition of claim 12, wherein the viscosity decreases when the temperature increases from about 20° C. to about 33° C., or to about the temperature of a lactating animal's udder.

14. The veterinary composition of claim 12, wherein the viscosity is about 4,000 to 5,000 Cp (at 20° C.); about 3,000 to about 4,000 (at 25° C.); and about 2,000 to about 3,000 (at 33° C.).

15. The veterinary composition of claim 12, wherein the viscosity is about 1300 to about 1500 (at 20° C.); about 900 to about 1,200 (at 25° C.); and about 600 to about 800 (at 33° C.).

16. The veterinary composition of claim 11 or 12, wherein the TRM is present in amount of about 1 to about 5% w/v of the composition.

17. The veterinary composition of claim 9, wherein the TRM is one that causes the composition to increase viscosity when the temperature is increased from about 20° C. to about 33° C., or to about the temperature of a lactating animal's udder.

18. The veterinary composition of claim 17, wherein the TRM is a poloxamer.

19. The veterinary composition of claim 1, wherein the composition is a paste.

20. The veterinary composition of claim 19, comprising the antimicrobial polyamide, a gel base, and a non-toxic heavy metal salt.

21. The veterinary composition of claim 20, wherein the gel base comprise liquid paraffin and the heavy metal salt comprises bismuth subnitrate.

22. The veterinary composition of claim 19, which comprises an antioxidant selected from the group consisting of alpha tocopherol, ascorbic acid, ascorbyl palmitate, fumaric acid, malic acid, sodium ascorbate, sodium metabisulfate, n-propyl gallate, BHA, BHT and monothioglycerol.

23. The veterinary composition of claim 19, which comprises a preservative selected from the group consisting of parabens, benzalkonium chloride, benzethonium chloride, benzoic acid, benzyl alcohol, bronopol, cetrimide, chlorhexidine, chlorobutanol, chlorocresol, cresol, imidurea, phenol, phenoxyethanol, phenylethyl alcohol, phenylmercuric acetate, phenylmercuric borate, phenylmercuric nitrate, potassium sorbate, sodium benzoate, sodium propionate, sorbic acid, and thimerosal.

* * * * *